(12) United States Patent
Hillwig

(10) Patent No.: US 7,854,946 B1
(45) Date of Patent: Dec. 21, 2010

(54) ANTI-INFLAMMATORY AND ANTI-HIV COMPOSITIONS AND METHODS OF USE

(75) Inventor: Matthew Lee Hillwig, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 271 days.

(21) Appl. No.: 12/129,391

(22) Filed: May 29, 2008

Related U.S. Application Data

(60) Provisional application No. 60/941,140, filed on May 31, 2007.

(51) Int. Cl.
*A61K 36/38* (2006.01)

(52) U.S. Cl. ...................................... 424/730

(58) Field of Classification Search ................ None
See application file for complete search history.

(56) References Cited

PUBLICATIONS

Recio et al. Screening of Tropical Medicinal Plants for Antiinflammatory Activity. Phytotherapy Research, vol. 9, pp. 571-574 (1995).*
Rocha et al. Antibacterial Phloroglucinols and Flavonoids From Hypericum Brasiliense. Phytochemistry. vol. 40. No. 5, pp. 1446-1452. 1995.*
Ishiguro et al. Saroaspidin A, B, and C: Additional Antibiotic Compounds from Hypericum Japonicum. Planta Medica. 1987. pp. 415-417.*
Roche et al. More Phloroglucinols from Hypericum Brasiliense. Phytochemistry. vol. 42. Issue 1. May 1996. Abstract. 3 pages.*
Hillwig, Matthew L., et al., "Better Understanding Bioactivity in Hypericum Species Through Metabolomics" Abstract and Poster from the Metabolics Society Third Annual Conference, Boston, MA, Jun. 25-28, 2006, 2 pages.

* cited by examiner

*Primary Examiner*—Patricia Leith
*Assistant Examiner*—Melenie McCormick
(74) *Attorney, Agent, or Firm*—McKee, Voorhees & Sease, P.L.C.

(57) ABSTRACT

The metabolic fingerprint and anti-inflammatory activity and anti-HIV activity of *H. gentianoides* is disclosed. High performance liquid chromatography (HPLC) analysis shows that *H. gentianoides* contains a family of compounds, including some not previously observed in other *Hypericum* species. *H. gentianoides* extracts and fractions from these extracts reduce prostaglandin E2 synthesis in mammalian macrophages and inhibit HIV in infected HeLa cells. The present invention provides extracts and fractions thereof from *H. gentianoides* for use in pharmaceutical compositions and methods for the treatment or inhibition of inflammation, prostaglandin E-mediated disease, disorder or condition, a cyclooxygenase-mediated disease, disorder or condition, or an HIV infection.

5 Claims, 24 Drawing Sheets

ANTI-INFLAMMATORY AND ANTI-HIV COMPOSITIONS AND METHODS OF USE

CROSS-REFERENCE TO RELATED APPLICATIONS

This application claims priority under 35 U.S.C. §119 of a provisional application Ser. No. 60/941,140 filed May 31, 2007, which application is hereby incorporated by reference in its entirety.

GRANT REFERENCE

This invention was made with government support under Grant No. P01 ES012020 and Grant No. 9P50AT004155-06 by the National Institutes of Health. The government has certain rights in this invention.

BACKGROUND OF THE INVENTION

The *Hypericum* genus contains over 450 species; the minority that have been chemically analyzed to date are rich in secondary metabolites such as flavonoids, xanthones, anthrones, dianthrones, and various benzophenone derivatives. Several of these species, most commonly *Hypericum perforatum*, are used as herbal treatments for anti-inflammatory, antibacterial, antiviral, and anti-depressive applications (Mennini, T. and M. Gobbi (2004), "The antidepressant mechanism of *Hypericum perforatum*" *Life Sciences* 75(9): 1021; and Rocha, L., A. Marston, et al. (1995), "Antibacterial phloroglucinols and flavonoids from *Hypericum brasiliense*" *Phytochemistry* 40(5):1447). The chemical diversity within this single species may explain these multiple medicinal uses. Phloroglucinols are of particular interest since they have multiple bioactivities themselves, including anti-bacterial activity (Rocha, L., et al. (1995)) and anti-depressive properties in humans (Laakmann, G.; Schuele, C.; Baghai, T.; Kieser, M. (1998), "St. John's wort in mild to moderate depression: the relevance of hyperforin for the clinical efficacy," *Pharmacopsychiatry* 31 (Suppl. 1), 54-59). A few known phloroglucinols found in *Hypericum* species include hyperforin, uliginosin A and B; and hyperbrasilol A, B, and C (Rocha, L., et al. (1995)).

Anti-inflammatory activity in mammals has been reported for more than one species from the *Hypericum* genus (Rabanal, R. M., C. X. Bonkanka, et al. (2005), "Analgesic and topical anti-inflammatory activity of *Hypericum canariense* L. and *Hypericum glandulosum* Ait," *Journal of Ethnopharmacology* 96(3):591; and Sanchez-Mateo, C. C., C. X. Bonkanka, et al. (2006), "Evaluation of the analgesic and topical anti-inflammatory effects of *Hypericum reflexum* L. fil," *Journal of Ethnopharmacology* 107(1):1); however, it is not known whether this is caused by the same compound(s) in these different species. This anti-inflammatory activity has been confirmed by both in vivo and in vitro studies in *Hypericum* and related genuses (Rabanal, R. M., C. X. Bonkanka, et al. (2005); and Yamakuni, T., K. Aoki, et al. (2006), "Garcinone B reduces prostaglandin E2 release and NF-[kappa]B-mediated transcription in C6 rat glioma cells," *Neuroscience Letters* 394(3):206). Extracts or compounds from *Hypericum* species *H. perforatum*, *H. laricifolium*, and *H. patulum* (El-Seedi, Hesham R., Ringbom, T., Torssell, K. and Lars Bohlin. (2003), "Constituents of *Hypericum laricifolium* and Their Cyclooxygenase (COX) Enzyme Activities," *Chem. Pharm. Bull.* 51:1439-1440), reduce cyclooxygenase activity and inducible nitrous oxide synthase activity in vitro (Raso, G. M., M. Pacilio, et al. (2002), "In-vivo and in-vitro anti-inflammatory effect of *Echinacea purpurea* and *Hypericum perforatum*," *Journal of Pharmacy and Pharmacology* 54:1379), indicating their direct effect on reducing inflammation.

A few North American species of *Hypericum* have been used historically for their medical properties; one such species is *H. gentianoides* (Hamel, Paul B., Chiltoskey, Mary U. 1975 *Cherokee Plants and Their Uses—A 400 Year History*, Sylva, N.C. Herald Publishing Co. 53 p). *H. gentianoides* (orangegrass) is a small perennial that is native to much of the eastern United States. The Cherokee Native Americans used this plant for the treatment of fever, gastrointestinal disorders, nosebleeds, sores, and venereal disease (Hamel, Paul B., et al. 1975). Despite its use by Native Americans, there has been very little biochemical research on this species.

BRIEF SUMMARY OF THE INVENTION

According to the invention, extracts from *H. gentianoides* reduce prostaglandin E2 synthesis in inflammation response induced mammalian macrophages and reduces HIV infection in human Hela cells. The metabolic fingerprint disclosed herein indicates that the *H. gentianoides* extract and fractions contain novel compounds.

Accordingly, the present invention provide methods for preparing an extract and fractions therefrom that have anti-inflammatory activity and/or anti-HIV activity. The extract or fractions may include one or more bioactive constituents that has a retention time of from about 28 to about 38 minutes, or preferably from about 30 to about 35 minutes, when performing HPLC using 150×4.6 mm column with a gradient at approximately 40° C. of about 85% of mobile phase A (10 mM ammonium acetate) and about 15% of mobile phase B (90% acetonitrile and 10% methanol v/v) for about 10 minutes, increasing to about 80% mobile A and about 20% mobile B, then increasing to about 100% mobile B in about 25 minutes, and holding at about 100% mobile B for about 5 minutes with a flow rate of about 0.75 mL/minutes gradient/minutes. One or more of the constituents absorbs ultra violet light (UV) at 230, 300 and 350 nanometers (nm) or at 226, 287, and 357 nm, has a mass to charge (m/z) ratio of 445, 459, 497, 499, 513, or 554 as detected using mass spectrometry and has anti-inflammatory or anti-HIV activity.

In one aspect, the invention involves the use of saroaspidin A, uliginosin B, uliginosin A, saroaspidin B or japonicin A, a first sterol, a first acyl-phloroglucinol, a second sterol, uliginosin A, a second acyl-phloroglucinol, or hyperbrasilol C isolated from *Hypericum* species in treatment of conditions involving inflammation or in treatment of HIV. In a more preferred embodiment, the invention involves the use of acyl-phloroglucinols from any source in the treatment of the same. The acyl-phloroglucinols preferably have a conserved ring structure that is shown in FIG. 18. In a most preferred embodiment, the acyl-phloroglucinols are one or more of saroaspidin A, uliginosin A, or hyperbrasilol C. These compounds may be synthesized or isolated from any source, but may optionally be obtained as purified constituents from *Hypericum*. species, preferably *H. gentianoides*.

Acyl-phloroglucinols of the invention, particularly saroaspidin A, uliginosin A, or hyperbrasilol C are all known and commercially available, as are methods for their synthesis, See, for example Miekle et al, *J. Chem. Soc. Chem. Commun.*, 1972, ppg 123-124, "Synthesis of the antibiotics uliginosin A and dihydrouliginosin B".

Accordingly, the present invention provides pharmaceutical compositions, and therapeutic treatments for the treatment or inhibition of inflammation, prostaglandin E2-mediated disease, disorder or condition, a cyclooxygenase-mediated disease, disorder or condition, or an infection of HIV.

The methods include administering to a subject a therapeutically effective amount of an extract, fraction thereof or compound thereof comprising an acyl-phloroglucinol or other active compound which may optionally be isolated from *H. gentianoides* according to the teachings herein. As discussed herein, the extract, fraction thereof or compound may be combined with a pharmaceutically acceptable carrier.

One or more of the extract, fractions or compounds of the invention may be combined for treating inflammation, a prostaglandin E2-mediated disease, disorder or condition, a cyclooxygenase-mediated disease, disorder or condition, or an infection of HIV or testing for anti-inflammatory or anti-HIV activity. Methods of treating as described herein can be applied to cells in vivo or those being cultured in vitro as well. This invention also provides pharmaceutical compositions comprising one or more of the extract, fractions thereof or compounds thereof in a pharmaceutically acceptable carrier.

Other aspects, objects and advantages of the invention will be apparent from the detailed description that follows.

DETAILED DESCRIPTION OF THE PREFERRED EMBODIMENT

It must be noted that, as used in this specification and the appended claims, the singular forms "a," "an," and "the" include plural referents unless the context clearly dictates otherwise.

Figure 18:
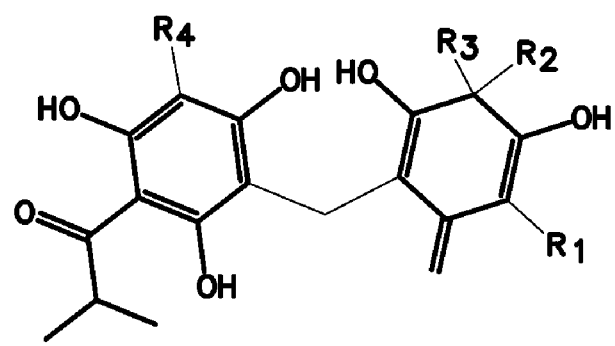
FIG. 18. Conserved structural regions amongst saroaspidin A, uliginosin A, and hyperbrasilol C. The left ring system is defined as an acyl-phloroglucinol and portion highlighted in red is conserved between all three compounds. The right ring system is defined as a filicinic acid moiety with a ketoacyl group located at $R_1$ or $R_2$ or $R_3$; and the portion highlighted in blue is also conserved amongst all three compounds. These two rings are bonded together by a methylene bridge. In saroaspidin A and uliginosin A, $R_1$ is an isobutyryl group. However, R1 could be other branch chain acyl groups such as an isovaleryl group.

The present invention is based on the surprising discovery that an extract or fraction thereof of *H. gentianoides* has anti-inflammatory and/or anti-HIV activity. Preliminary spectrometric data indicate the presence of at least one novel compound or constituent. The terms constituent or compound are used herein interchangeably. The invention also includes the discovery of the active components of this extract which include the use of acyl-phloroglucinols in the treatment of the same. The acyl-phloroglucinols preferably have a conserved ring structure that is shown in FIG. 18. In a most preferred embodiment, the acyl-phloroglucinols are one or more of saroaspidin A, uliginosin A, or hyperbrasilol C. These compounds may be synthesized or isolated from any source, but may optionally be obtained as purified constituents from *Hypericum*. species, preferably *H. gentianoides*.

The present invention relates to extracts or fractions thereof from a plant, for example, *H. gentianoides*, that have anti-inflammatory and/or anti-HIV activity activity.

The present invention also relates to fractions obtained from liquid chromatography that have anti-inflammatory or and anti-HIV activity. In specific embodiments, the invention also includes compounds isolated from the extract or fraction thereof. Accordingly, the present invention provides methods for preparing and identifying extracts and fractions thereof and compounds thereof that have anti-inflammatory or anti-HIV activity.

The present invention further relates to therapeutic methods and compositions for treatment of a disease, disorder, or condition associated with inflammation, a prostaglandin-mediated or a cyclooxygenase (COX)-mediated disease, disorder, or condition, or an HIV infection. Accordingly, the invention provides for treatment of inflammation, a prostaglandin-mediated disease, disorder, or condition, a cyclooxygenase (COX)-mediated disease, disorder, or condition, or an HIV infection by administration of therapeutically effective amount of a plant extract, fraction thereof or compound thereof or by administration of an effective amount of an acyl-phloroglucinol compound preferably with a conserved ring structure that is shown in FIG. 18. In a most preferred embodiment, the acyl-phloroglucinols are one or more of saroaspidin A, uliginosin A, or hyperbrasilol C from any source.

The pharmaceutical compositions of the invention include extracts, fractions or compounds thereof of the present invention. Also contemplated are pharmaceutical compositions comprising a plant extract or fraction thereof or compound identified from the fraction such as acyl-phloroglucinols preferably with a conserved ring structure that is shown in FIG. 18. In a most preferred embodiment, the acyl-phloroglucinols are one or more of saroaspidin A, uliginosin A, or hyperbrasilol C from any source, including related derivatives and analogs of the compounds.

In one aspect, the present invention provides for a method of identifying an extract, a fraction or compound(s) from a plant of the *Hypericum* genus or *H. gentianoides* species that has anti-inflammatory activity and/or anti-HIV activity. The method includes introducing an extract from the plant into a high performance liquid chromatography column.

Plant material may be acquired from commercial sources, for example, USDA North Central Regional Plant Introduction Station (Ames, Iowa). *Hypericum* extracts, for example from *H. gentianoides*, as starting materials for the chromatographic processes described herein may be obtained by any suitable extraction technique. In one aspect, a method of the present invention includes obtaining a plant extract. Extracts can be prepared using any suitable method including these described herein. Any part of the plant may be used as a source for the extract, for example, the upper aerial portion of the mature flowering plant, for example, the flowering top. The plant material used may be dried or fresh.

An extract may be prepared from a plant or plant material, using any number of methods, for example, liquid nitrogen and solvent extraction. See Example 1. In one aspect, the plant material is made into a concentrated extract. The plant material may be frozen, for example, using liquid nitrogen, and ground prior to extraction. In one aspect, the plant material is extracted by immersion of the plant material in an organic or hydrophilic solvent, for example, methanol or ethanol, such as 70% ethanol. Any miscible solvent such as short chain alcohols or acetone or hexanes that produce a homogeneous solution of the solvent and the compounds of interest may also be used. The solvent may be at a temperature in the range of −4 to 4° C. The ground plant material, such as the tissue, in the organic or hydrophilic solvent may be dissolved using sonication techniques. In one aspect, the extract may be concentrated by separating insoluble plant material from the dissolved extract by using centrifugation and filtration of the supernatant. The organic solvent may be evaporated from the tissue under conditions that prevent oxidation of acyl-phloroglucnois, for example, under nitrogen gas at 40° C. so that the sample remains stable while the solvent is evaporated. Preferably, the temperature during evaporation does not exceed 40° C.

The extract may be dried and optionally dissolved in a solution, for example, in a solution of 70% mobile phase B and 30% mobile phase A, or DMSO, prior to introduction into a HPLC column. The present inventor has found that four grams of dry plant material will yield approximately one gram of extract or extracted constituents.

In one aspect of the method, the extract may be separated into fractions. As described herein, a variety of chromatographic procedures can be used to isolate fractions containing the compounds that have anti-inflammatory activity and/or anti-HIV activity.

Any suitable technique for separating molecules may be used. Such chromatographic processes include HPLC, reverse-phase HPLC, and ion-exchange chromatography. In one aspect, the chromatographic procedure is HPLC. In one aspect, solid-phase extraction could be used to semi-purify the active constituents prior to fractionation by semi-preparative HPLC.

In one aspect, the method includes using a combination of two solutions, referred to herein as mobile phase A and mobile phase B, that have differing amounts of organic solvents. Both mobile phases comprise an organic solvent. Typically, the percentage of organic solvent in mobile phase A will be lower than the percentage of the organic solvent in mobile phase B. Any suitable organic solvent, such as a suitable organic salt dissolved in water or another suitable solvent, may be used and includes but is not limited to ammonium acetate or ammonium formate. In one aspect, mobile phase A comprises 10 mM ammonium acetate or ammonium formate. In another aspect, mobile phase B comprises 90% v/v acetonitrile and 10% methanol.

In another aspect, the method includes eluting the column with an increasing linear gradient of organic solvent (i.e., mobile phase B) to elute the molecules or combinations thereof. Elution can be performed using one or more gradients or isocratic conditions, with gradient conditions preferred to reduce the separation time and to improve resolution. Generally, the gradient comprises solvents from very low organic content (from about 10%, preferably from about 13%) to very high organic content (up to 100%). A particularly preferred method involves the use of a linear gradient of about 13% to about 15% B in about 10 minutes, increasing to about 15% to about 100% B in about 30 minutes, and then increasing to about 100% B for about 5 minutes at about 40°

C. at a flow rate of about 4.6 ml/min. (Example 2) The slow rise from 13% to 15% over 10 minutes optimizes the separation of more polar phenylpropanoids from later eluting flavonoids followed by acylphloroglucinols. While a range of flow rates from 3-5 mL/min were tested, a flow rate of 4.6 mL/min optimized separation of compounds and matched retention times with the analytical method within 3 min or less.

In one aspect, the chromatography column comprises a $C_{12}$ silica-derivatized stational phase. In one aspect, the column is a Synergy Max-RP column (Phenomenex, Torrance, Calif.). In one aspect, the column dimension is 250×10 mm. It is understood that any chromatography column suitable for separating the extract into fractions may be used in the methods of the present invention. The columns may vary in diameter, length or both, for example, to accommodate larger or smaller sample sizes. Flow rates can vary depending on the column, without limitation, from 0.1 to 1 ml/minute. As demonstrated herein, the flow rate for the mobile phase was 4.6 ml/minute. However, the flow rate of the mobile phase can be altered as desired. A slower flow rate, such as 1 μl/minute, 10 μl/minute or 100 μl/minute, can be used, for example, with a smaller column or a nanocolumn or to increase separation of fractions.

Column size, flow rates, and conditions (e.g. pH, choice of buffer) are selected in accordance with standard techniques and may be optimized for both chromatographic separation and electrospray ionization efficiency. Those skilled in the art will appreciate, and readily accommodate, without undue experimentation, that adjusting flow rates and gradients for substitution of various A/B gradient setups, such as substituting water/acetonitrile for water/methanol. Even so, specific percentages, times and flow rates will readily be selectable for various choices of solvents, all in accordance with the teachings disclosed herein.

In one aspect, the method includes testing the extract, fraction or compound thereof for anti-inflammatory activity or anti-HIV activity. Effectiveness of the extract, fraction, or compounds isolated thereof of the invention for treatment or inhibition of inflammation, a prostaglandin-mediated disease, disorder or condition mediated for example by PGE2, or cyclooxygenase (COX)-mediated disease (COX), disorder or condition mediated for example by COX-2, or HIV infection can be determined in vitro or in vivo by any of the methods disclosed herein or by any method known in the art.

Efficacy of the extracts, fractions, or compounds thereof can be assessed by any method for assessing inflammation, PGE2 or COX level or activity, or HIV activity, for example, HIV replication or inhibition of HIV infection. It is known that COX-2 is induced during the inflammatory response (DeWitt D L, Biochim Biophys Acta, 1083:121 34, 1991; Seibert et al., Receptor, 4:17 23, 1994). There are many known methods for assessing inflammation including without limitation, use of contrast ultrasound in conjunction with injection of microbubbles, measurement of inflammatory cytokines (such as TNF-α, IL-1, IFN-γ), measure of activity or level of enzymes or compounds associated with inflammation or known to be pro-inflammatory (prostaglandins such as PGE2, COX-2, COX-1, thromboxanes and prostacyclins), measurement of activated immune system cells as well as observation (reduction of oedema, reduction of erythema, reduction of pruritus or burning sensation, reduction of body temperature, improvement in function of the afflicted organ) as well as any of the methods provided below. See U.S. Pat. No. 7,109,176 to Mercep et al., herein incorporated in its entirety.

As shown in Example 2, anti-inflammatory activity of an extract, fraction or compound thereof of the present invention may be determined by subjecting a macrophage to lipopolysaccharide (LPS) and an extract, fraction or compound thereof and measuring levels of prostaglandin E2 (PGE2), for example, compared to levels of PGE2 in LPS treated macrophages not administered the extract, fraction or compound thereof. The supernatant may be assayed to determine levels of PGE2 released from the cell. Evaluation of the PGE2 production may be by any means known, including quantitation of the PGE2 (e.g., with ELISA), or by bioassay, (e.g. determining whether PGE2 activity is reduced).

The ability of the extracts, fractions, and compounds of this invention to reduce PGE2 or COX-1 or COX-2 levels or activity or combinations thereof may be determined, for example, by measuring the amount of PGE2 synthesized in the presence of LPS, arachidonic acid, cyclooxygenase-1 or cyclooxygenase-2 and an extract, fraction thereof or compound thereof of the present invention. See Example 2.

Figure 9:
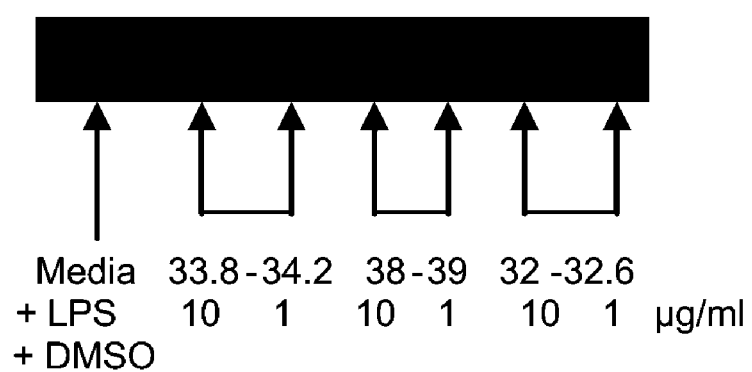
FIG. 9. The western blot shows a reduction of cyclooxygenase-2 enzyme in LPS-induced macrophages treated with *H. gentianoides* fractions 38-39 min and 32-32.6 min, isolated with the semi-preparative HPLC method. After an 8 hour treatment with lipopolysaccharide (LPS) and *H. gentianoides* fractions, a protein extraction was performed on the RAW 264.7 macrophages. Separation of the proteins was carried out on a discontinuous (4% stacking, 10% resolving) sodium dodecyl sulfate-polyacrylamide (30% acrylamide/bis solution) (BioRad; Hercules, Calif.) gel, followed by transfer to a PVDF membrane (GE Healthcare; Piscataway, N.J.) at 100V for 2.5 hours. COX-2 rabbit polyclonal antibody (Santa Cruz Biotechnology, Santa Cruz, Calif.) was diluted 1:1000 in 5% milk Tris-buffered saline with 0.5% Tween-20 (TBS-T). The secondary antibody (goat, anti-rabbit IgG, HRP conjugated, Santa Cruz Biotechnology; Santa Cruz, Calif.) was diluted 1:1000 in 5% milk in TBS-T. Detection was visualized on blue sensitive autoradiographic film (Marsh Bioproducts; Rochester, N.Y.) with a chemiluminescence (ECLplus) detection kit (GE Healthcare; Piscataway, N.J.).

According to the invention, extracts of *H. gentianoides* may possess selective COX-2 inhibitory activity as demonstrated by Western blot analysis in FIG. 9. In one embodiment of the present invention, a method for decreasing prostaglandin 2E (PGE2) and/or cyclooxygenase (COX) levels or activity, for example, COX 1 or 2, is disclosed which employs administering a preparation including an extract, fraction thereof or compound thereof of the present invention. In one aspect, the extract, fraction thereof or compound thereof has anti-inflammatory activity.

The inhibitory effects of the whole extract and a fraction thereof (fraction 2) isolated from *H. gentianoides* on Human Immunodeficiency Virus (HIV) activity, specifically, their inhibitory activity on HIV infection are also disclosed. See Example 6. As used herein, "inhibiting HIV infection" or "inhibition of HIV infection" means reducing the amount of HIV genetic information introduced into a target cell population as compared to the amount that would be introduced in absence of the extract, fraction, compound or composition of the present invention.

This invention provides a method for identifying an extract, fractions thereof or compounds thereof from *H. gentianoides* that inhibits HIV infection, for example, HIV-1 or HIV-2 infection. In one aspect, the method includes contacting an effective amount of extract, fraction thereof or compounds thereof with a cell with a CD4 receptor (CD4+ cell), for example, a monocyte or macrophage cell, exposed to HIV and comparing the amount of HIV infection with the control that does not receive the addition of the extract, fraction or compound. A decrease in HIV infection of the cells indicates that the extract, fraction or compound is capable of inhibiting HIV infection. This invention also includes extracts, fractions or compounds identified by the above method. The extract, fractions or compounds of the invention may also be assayed for HIV reverse transcriptase (RT) activity using for example an assay based on the technique of Willey et al herein incorporated by reference. (Willey, R. L., Smith, D. H., Lasky, L. A., Theodore, T. S., Earl, P. L., Moss, B., Capon, D. J. & Martin, M. A. (1988) Journal of Virology 62, 139-47.) In one aspect, the method includes contacting a therapeutically effective amount of the extract, fraction thereof or compounds thereof with a cell with a CD4 receptor (CD4+ cell), for example, a monocyte or macrophage cell, exposed to HIV and comparing the amount of reverse transcriptase (rt) activity with the control that does not receive the addition of the extract, fraction or compound. A decrease in rt activity of the HIV indicates that the extract, fraction or compound is capable of inhibiting reverse transcriptase in a cell. This invention also provides a pharmaceutical composition comprising one or more of the extracts, fractions or compounds identified by any of the above methods and a pharmaceutically acceptable carrier. In another embodiment, the present invention relates to a method of inhibiting HIV infection of a CD4+ cell exposed to HIV. The method also involves the administration of a therapeutically effective amount of the an extract, fraction thereof or compound thereof of the present invention to a subject in need of such treatment. This invention provides a method of inhibiting HIV infection in a subject comprising administering an effective amount of the extract, fraction thereof or compound thereof of the present invention or a pharmaceutical composition described herein to the subject. The methods of using the extract, fraction thereof or compound thereof of or pharmaceutical compositions of the present invention are not particularly limited, and may be used in vivo, in vitro, ex vivo for the inhibition of HIV infection of monocytic cells exposed to HIV. The compositions and methods of therapy of the present invention are useful in the inhibition of HIV infection, the prevention or treatment of infection by HIV or diseases, disorders, or conditions associated with HIV infection. These include but are not limited to AIDS, Kaposi's sarcoma, opportunistic infections such as those caused by *Pneumocystis carinii* and *Mycobacterium tuberculosis*; oral lesions, including thrush, hairy leukoplakia, and aphthous ulcers; generalized lymphadenopathy, shingles, thrombocytopenia, aseptic meningitis, and neurologic disease such as toxoplasmosis, cryptococcosis, CMV infection, primary CNS lymphoma, and HIV-associated dementia, peripheral neuropathies, seizures, and myopathy. Animal models of HIV infection for testing the efficacy of the extracts, fractions or compounds of the invention may also be used. It is also contemplated that the methods and compositions of the present invention may be used in conjunction with other lentivirus such as simian immunodeficiency virus (SIV) and feline immunodeficiency virus (FIV) in addition to HIV-1, HIV-2 and used to treat diseases and disorders associated with various lentiviruses.

According to the invention, a compound can be identified from the components of the whole extract or a fraction thereof by any of a variety or combination of methods including chromatographic and spectrometric methods. The present invention employs techniques, for example, HPLC, spectroscopy, and spectrometry that are routine using analytical methods of chemistry and biochemistry and that are well within the skill of the art. Such techniques are known and explained fully in the literature. See, e.g. "Mass Spectrometry: A Foundation Course", K. Downard, Royal Society of Chemistry, UK, 2004.; "An Introduction to Biological Mass Spectrometry", C. Dass, Wiley, USA, 2002; "Ionization Methods in Organic Mass Spectrometry", A. E. Ashcroft, Analytical Monograph, Royal Society of Chemistry, UK, 1997; "HPLC: A Practical User's Guide" 2nd edition, M. McMaster, Wiley, USA, 2006.; "LC/MS: A Practical User's Guide" M. McMaster, Wiley, USA, 2005; and "Modern HPLC for Practicing Scientists", M W Dong, Wiley, USA, 2006.

The present invention provides for at least nine compounds identified using methods of the present invention. See FIG. 7. In one aspect, a fraction containing at least one compound that has anti-inflammatory activity or anti-HIV activity may be obtained by any number of ways. In preferred embodiments the compounds are acyl-phloroglucinols preferably with a conserved ring structure that is shown in FIG. 18. In a most preferred embodiment, the acyl-phloroglucinols are one or more of saroaspidin A, uliginosin A, or hyperbrasilol C.

In one aspect, the method includes performing HPLC on the *H. gentianoides* extract using 250×10 mm column using a linear gradient comprising of from about 13 to about 15% mobile phase B in about 10 minutes, increasing to about 15% to about 100% mobile phase B in about 30 minutes, and then increasing to about 100% mobile phase B for about 5 minutes at about 40° C. at a flow rate of about 4.6 ml/min to separate the extract into two fractions.

In one aspect, the method includes subjecting the *H. gentianoides* extract to HPLC using 150×4.6 mm column with a gradient at about 40° C. of about 87% of mobile phase A (10 mM ammonium acetate) and about 13% of mobile phase B (90% acetonitrile and 10% methanol v/v) for about 10 minutes, increasing to about 83% mobile A and about 17% mobile B, then increasing to about 100% mobile B in about 25 minutes, and holding for about 5 minutes. The flow rate was 1.0 mL/minutes gradient.

In another aspect, the method includes subjecting the *H. gentianoides* extract to HPLC using 150×4.6 mm column with a gradient at about 40° C. of about 85% of mobile phase A (10 mM ammonium acetate) and about 15% of mobile phase B (90% acetonitrile and 10% methanol v/v) for about 10 minutes, increasing to about 80% mobile A and about 20% mobile B, then increasing to about 100% mobile B in about 25 minutes, and holding at about 100% mobile B for about 5 minutes. The flow rate was 0.75 mL/minutes gradient.

Use of these methods produces two fractions, fractions 1 and 2. See FIG. 4. It will be understood by one skilled in the art that use of these methods can be modified to produce as many fractions as desired for the experiment, for example several one-minute intervals may be collected for separating the extract further into individual components for further bioactivity guided fractionation.

In one aspect, the fractions or compounds may be assayed for anti-inflammatory activity as associated with PGE2 levels using LPS-induced macrophages as described in Example 2 or for inhibition of HIV infection as described in Example 6. Alternate methods to assay for inflammatory activity of PGE2 synthesis or COX activity, such as COX-2 activity, (e.g., direct measurement of PGE2 with analytical separation methods) may be used and would be understood to be usable in the assay of the fraction. Other methods may include microarray analysis of mRNA expression libraries to access changes in the co-expression of associated genes regulating COX-2 activity in the LPS-induced macrophages. Also, COX enzyme concentrations, for example, of COX-1 or COX-2, could be measured using tandem/time-of-flight mass spectroscopy. Furthermore, total metabolite nuclear magnetic resonance studies could be used to identify biomarker metabolites in the macrophages, associated with a change in response to LPS-induced inflammation when treated with anti-inflammatory *H. gentianoides* compounds. This would help identify the same response in other studies on the prevention of inflammatory responses.

Figure 5:
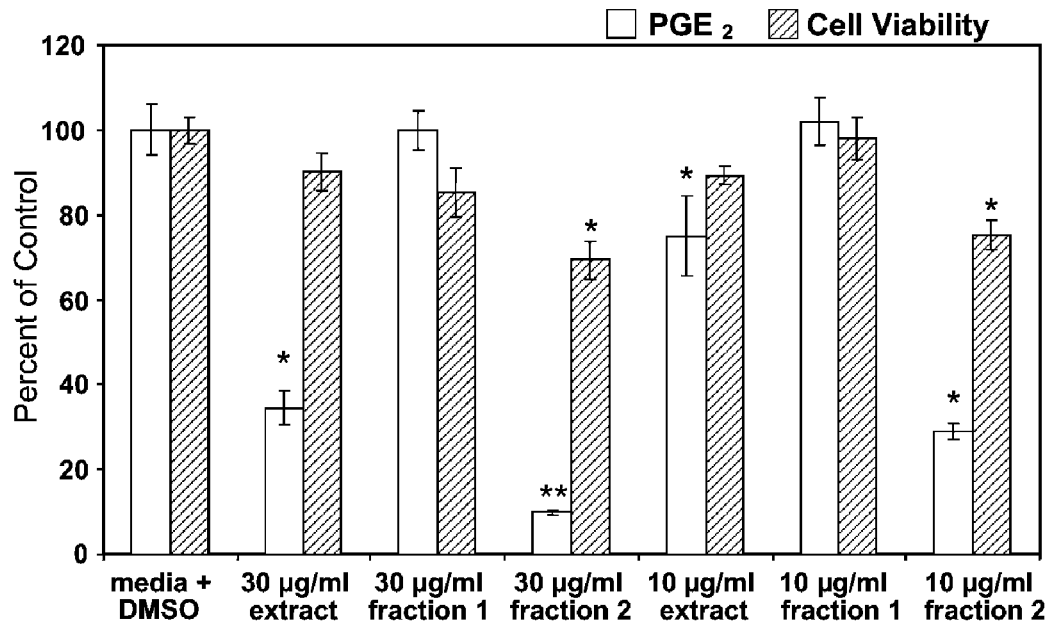
FIG. 5. Fraction 2 contains the anti-inflammatory activity for LPS induced macrophages at the tested doses. Decreased percent of control for PGE2 treated cells indicates increased anti-inflammatory activity. Anti-inflammatory activity (mean percent of media+DMSO+LPS PGE2 level±standard error) and cytotoxicity (mean percent of media+DMSO cell viability±standard error) of *H. gentianoides* fractions (n=4 for each). The concentration tested in μg/ml represents the final concentration of the extract in the media. Addition of LPS to the culture media+DMSO control increased the level of PGE2 18 fold over media+DMSO control alone (0.11±0.02 ng/ml for media+DMSO, 1.9±0.4 ng/ml for media+DMSO+LPS). Extracts in the culture media without LPS did not affect the concentration of PGE2 as compared to the media+DMSO control. * p-value less than 0.05 as compared to control. ** p-value less than 0.0001 as compared to control.
Figure 6:
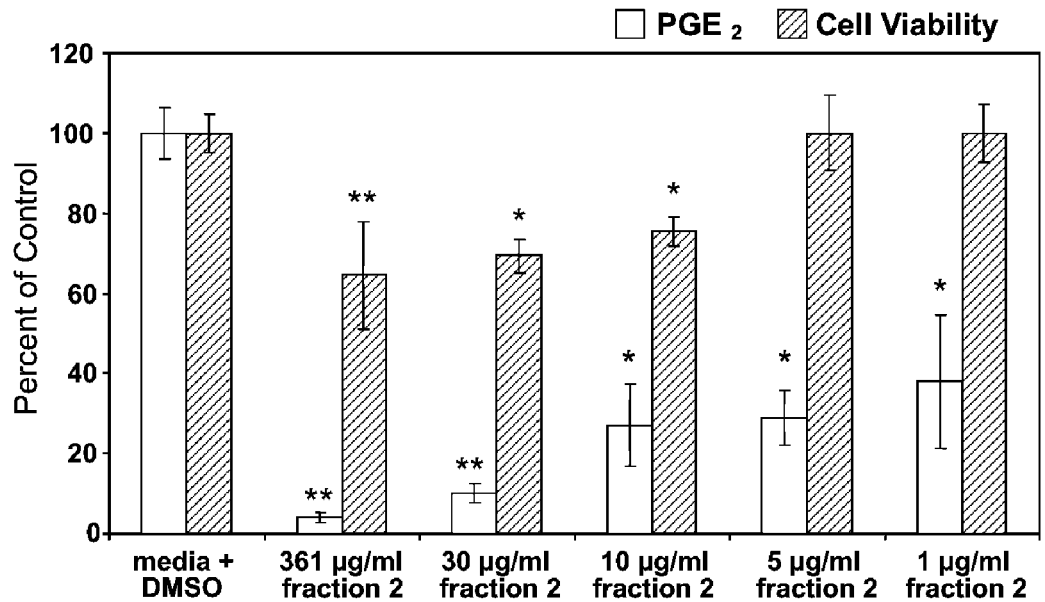
FIG. 6. The *H. gentianoides* extract Fraction 2 significantly reduced PGE2 concentrations in LPS-induced macrophages even at doses as low as 1 μg/mL. There was no significant cytotoxicity at concentrations of 5 μg/mL or less. Decreased percent of control for PGE2 treated cells indicates increased anti-inflammatory activity. Anti-inflammatory activity (mean percent of media+DMSO+LPS PGE2 level±standard error) and cytotoxicity (mean percent of media+DMSO cell viability±standard error) of *H. gentianoides* fraction 2 (n=4 for each). The concentration tested in μg/ml represents the final concentration of the extract in the media. Addition of LPS to the culture media+DMSO control increased the level of PGE2 18 fold over media+DMSO control alone (0.10±0.01 ng/ml for media+DMSO, 1.9±0.26 ng/ml for media+DMSO+LPS). Extracts in the culture media without LPS did not affect the concentration of PGE2 as compared to the media+DMSO control. * p-value less than 0.05 as compared to control. ** p-value less than 0.0001 as compared to control.
Figure 7A:
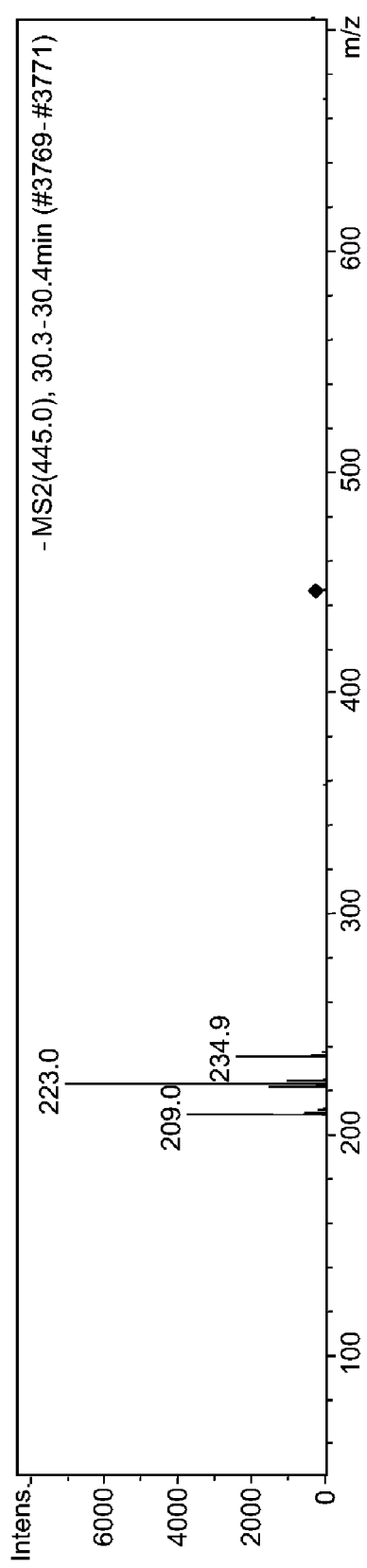
FIG. 7. The mass spectra data of particular molecular ions resulting from fragmenting the most abundant compounds found in the bioactive portions of the *H. gentianoides* methanol extract at MS/MS with an Agilent Ion Trap 1100 are shown. Based on the daughter ions observed, the proposed identities for some of the most abundant compounds found in the bioactive portions of the *H. gentianoides* methanol extract include (A) m/z 445-saroaspidin A, (B) m/z 497—uliginosin B, (C) m/z 459—saroaspidin B or japonicin A, (D) m/z 513—a sterol, (E) m/z 499—an acyl-phloroglucinol, (F) m/z 513—a sterol, (G) m/z 499—uliginosin A, (H) m/z 513—an acyl-phloroglucinol, (I) m/z 554—hyperbrasilol C. These mass spectra 'fingerprints' are reproducible fragmentation patterns capable of validating the presence of the compound in another extract. Many of these compounds appear to be acyl-phloroglucinols based on retention time in liquid chromatography methods and UV absorption maxima.
Figure 7B:
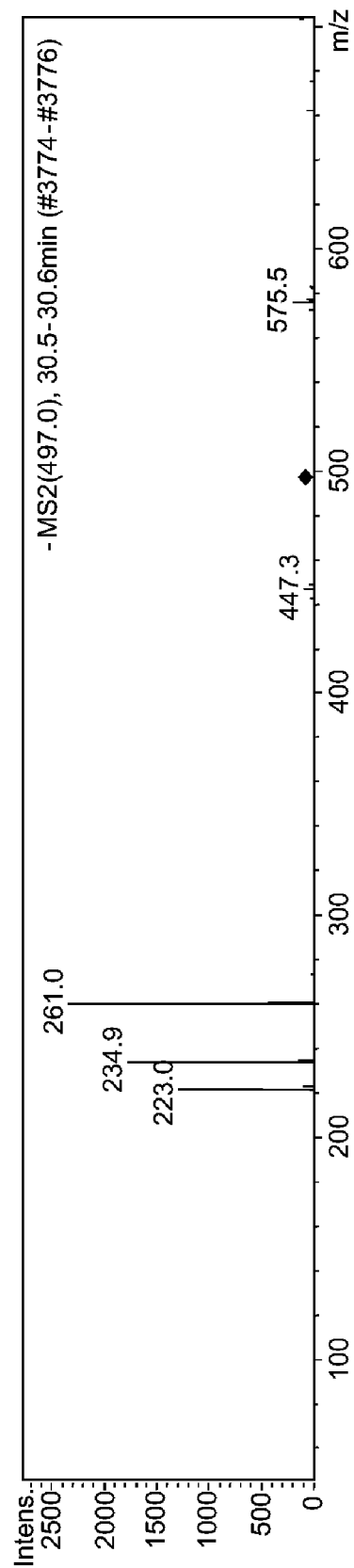
Figure 7C:
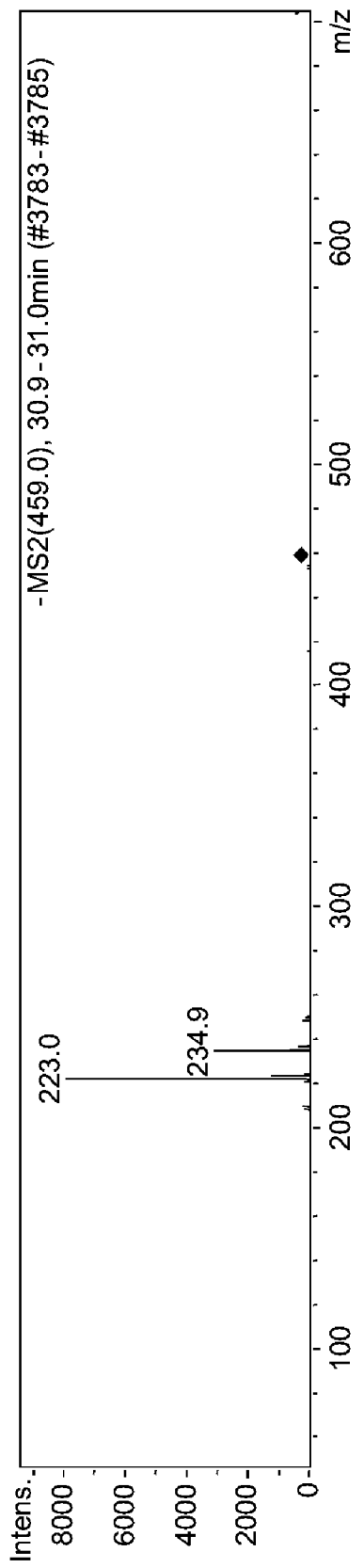
Figure 7D:
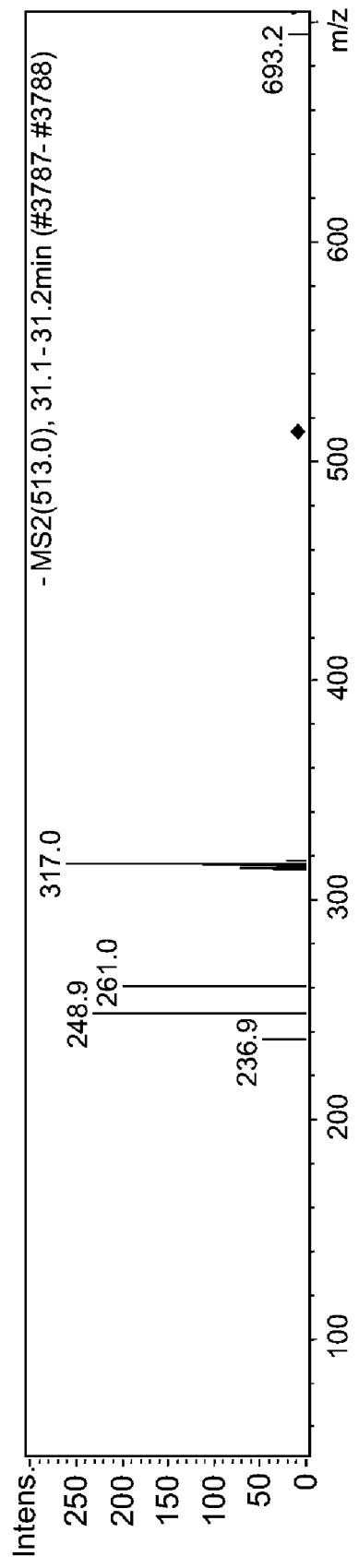
Figure 7E:
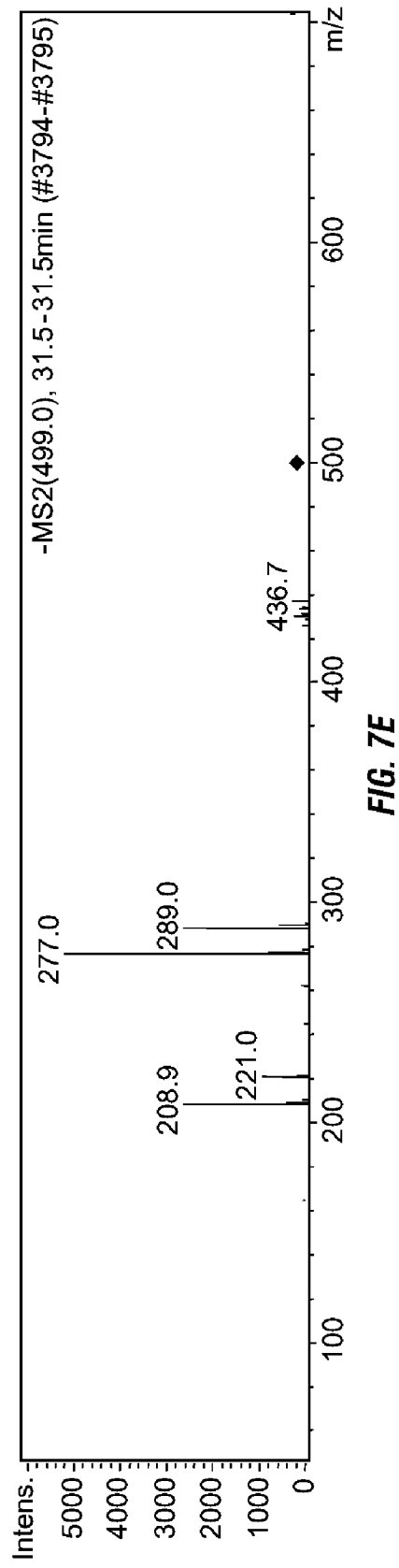
Figure 7F:
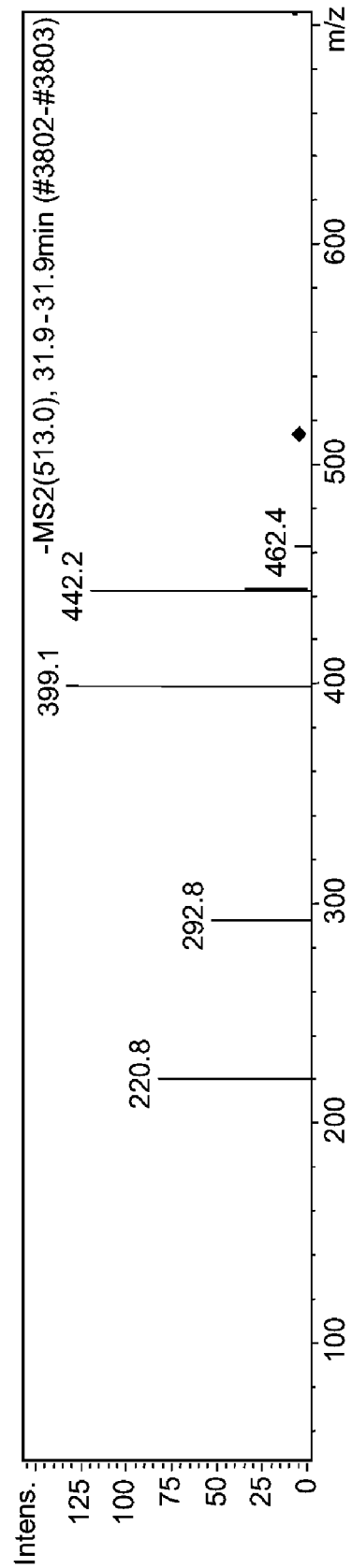
Figure 7G:
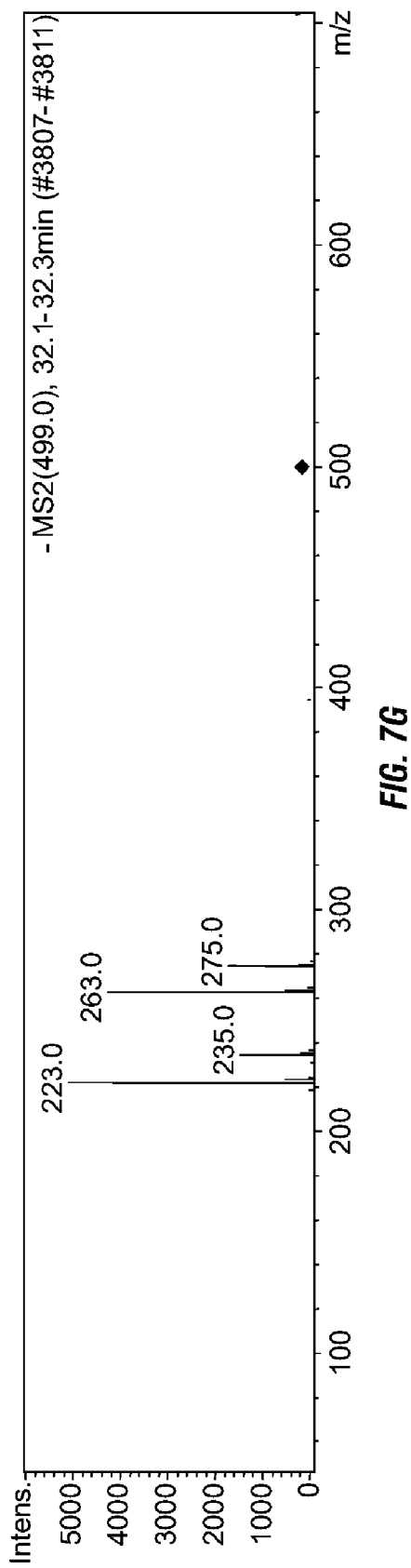
Figure 7H:
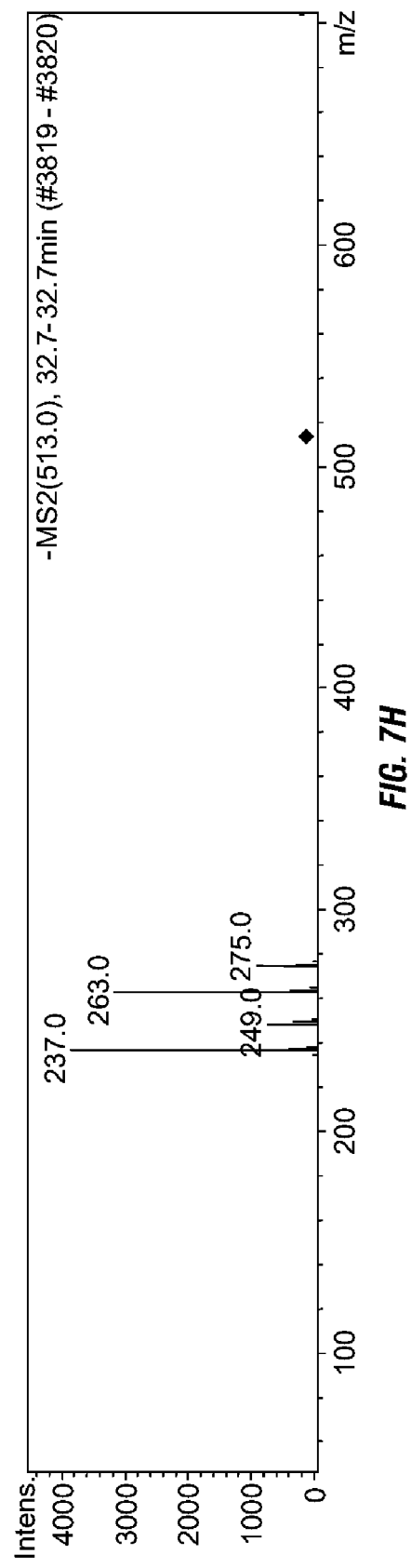
Figure 7I:
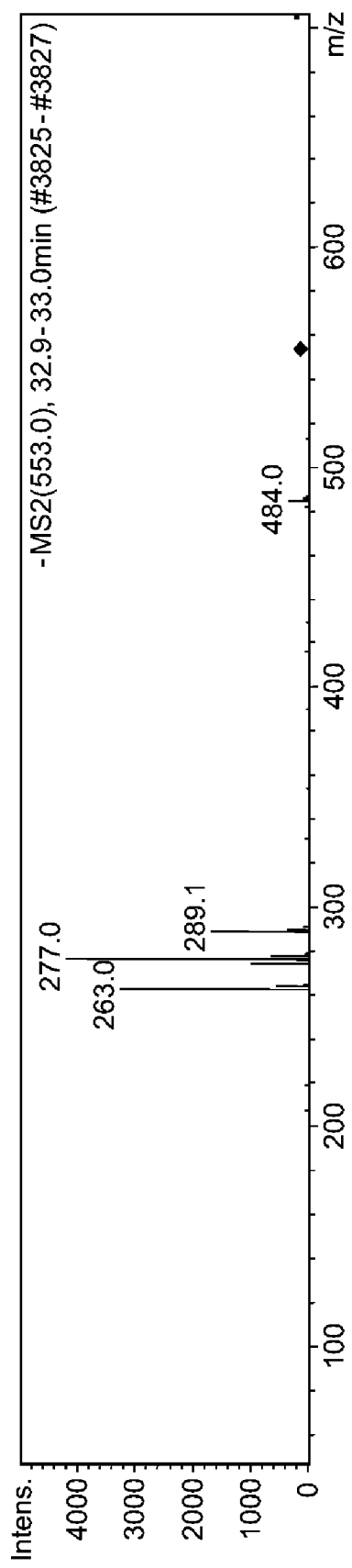

As demonstrated, fraction 2 reduced PGE2 concentration at every dose tested ranging from 30 μg/mL to 10 μg/mL, while fraction 1 did not reduce the PGE2 concentration at similar doses. This indicated that the active constituents are in fraction 2 (FIG. 5). Further testing revealed that fraction 2 significantly reduces PGE2 concentrations at a dose at 1 μg/mL (FIG. 6). The whole extract of *H. gentianoides* and fraction 2 was also found to reduce HIV infection of HeLa cells. See Example 6 and FIG. 8. As described herein, the fractions or compounds may be assayed for HIV inhibitory activity, such as HIV infection.

Fraction 1 or fraction 2 or both may be subjected to HPLC coupled to electrospray ionization mass spectrometry (ESI-MS) to further characterize the compounds/molecules, including, for example, individual retention times. See FIG.

Figure 1A:
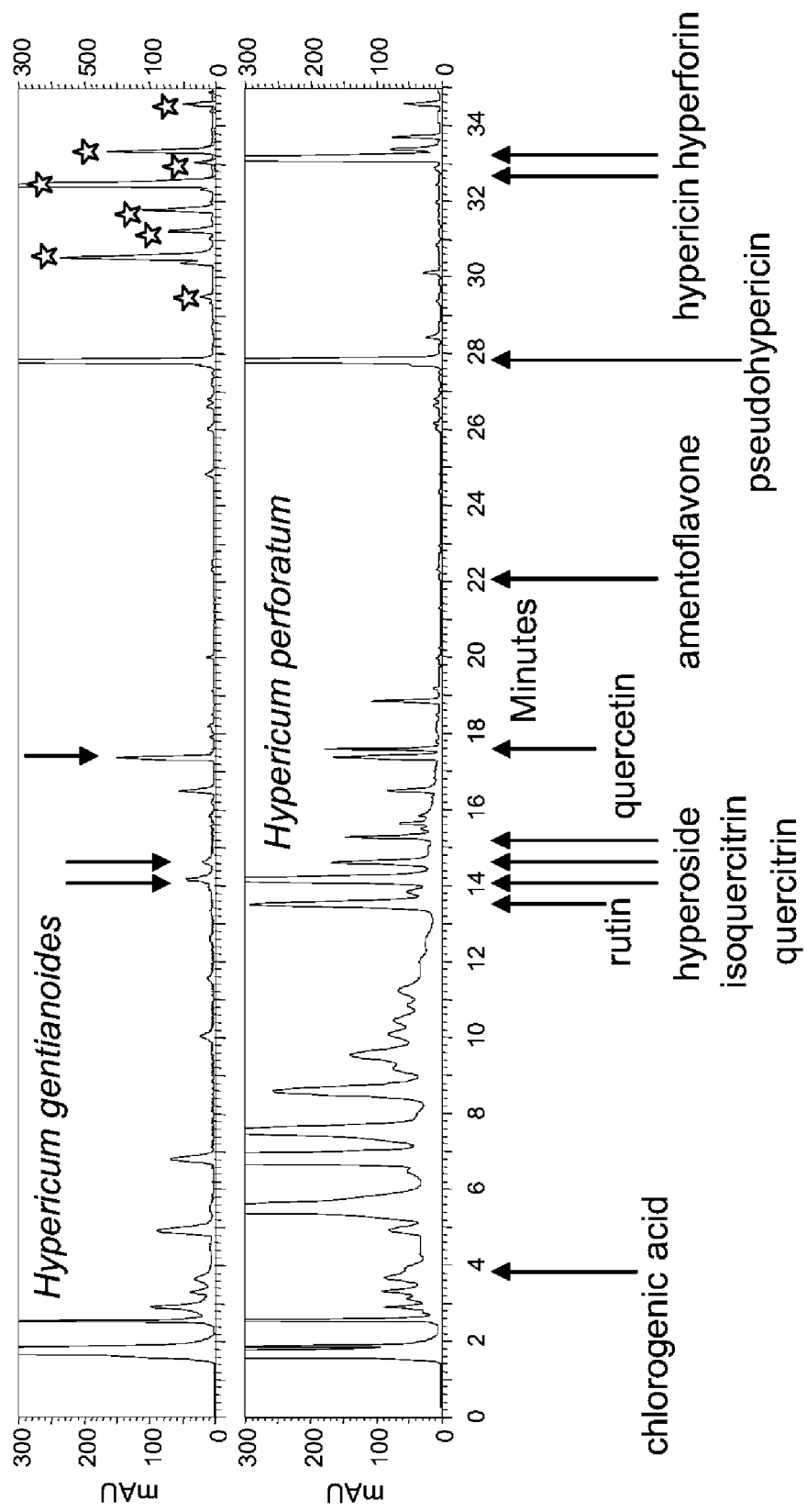
FIG. 1. (A) This HPLC chromatograph of a *H. gentianoides* extract shows the absence of many typical secondary metabolites found in the heavily studied *H. perforatum*. In the *H. perforatum* chromatograph pseudohypericin overlaps with flavonone, an internal standard added during initial screening extracts, eluting at retention time 27.5 min. It is this flavonone internal standard peak that appears in the *H. gentianoides* extract at 27.5 min. The HPLC-PDA indicates that *H. gentianoides* contains a distinct set of metabolites (constituents) not found in *H. perforatum* (indicated with stars). (B) The UV absorption fingerprints of the unknown compounds of interest show great similarity to one another. This suggests they are all related biosynthetically. UV absorption may be determined using UV spectroscopy and other methods known to one skilled in the art.
Figure 1B:
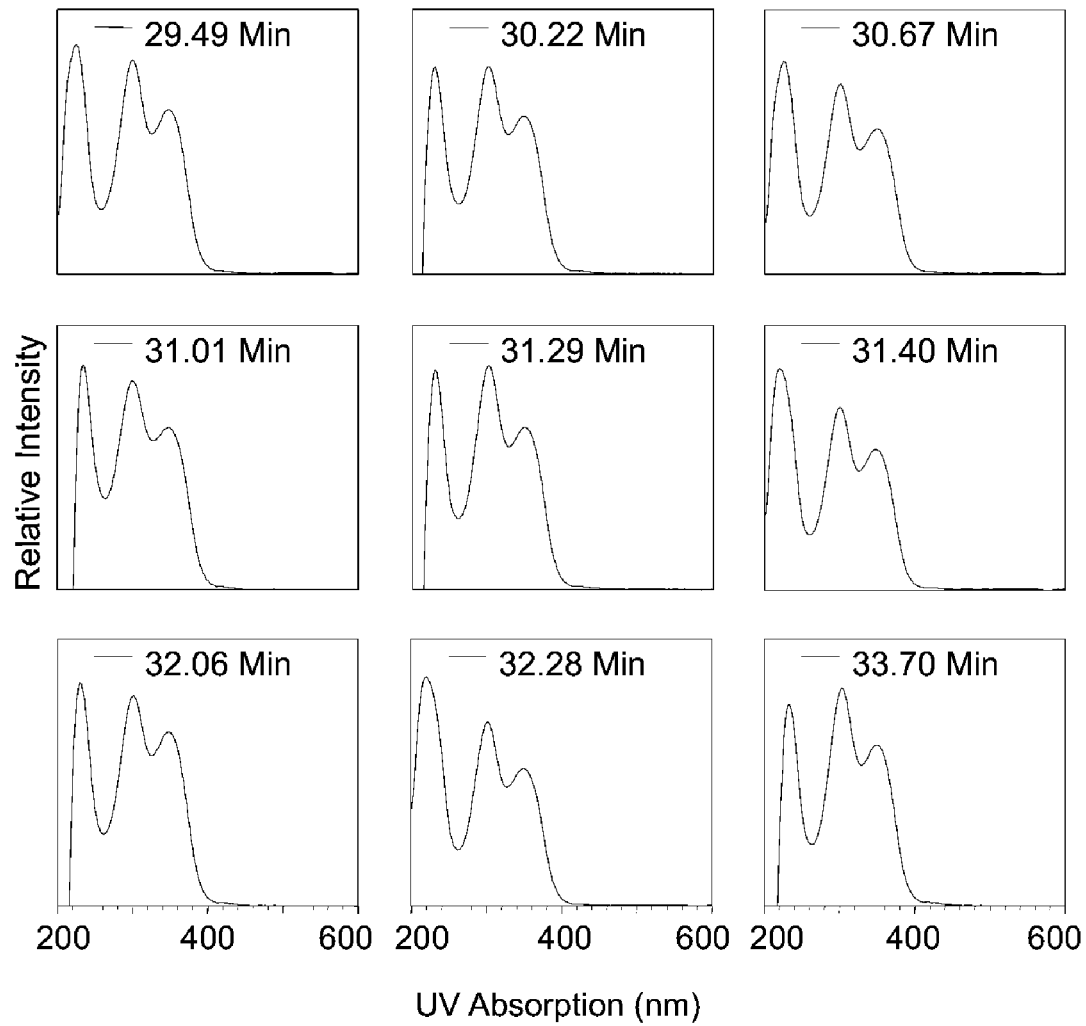

1B. The retention times for all anti-inflammatory compounds were between about 28 to about 38 minutes using the LC-MS method, gradient and conditions described herein. See also FIG. 2 and Example 1. More specifically, as shown in FIG. 1B, the molecules of fraction 2 have individual retention times of 29.49 minutes, 30.22 minutes, 30.67 minutes, 31.01 minutes, 31.29 minutes, 31.40 minutes, 32.06 minutes, 32.28 minutes, and 33.70 minutes.

In one aspect, at least one fraction of the extract may subjected to UV spectroscopy to further identify the compounds. (See R. M. Silverstein, G. C. Bassler and T. C. Morrill, *Spectrometric Identification of Organic Compounds,* 5th Ed., Wiley, 1991 incorporated herein in its entirety.) For example, the compounds of fraction 2 absorb UV at 230, 300 and 350 nanometers (nm) or at 226, 287, and 357 nm. Without wishing to be bound by this theory, it is believed that the UV absorption maxima and the retention time of these compounds is consistent with at least one of the compounds being an acyl-phloroglucinol.

It is understood that such analytical techniques such as HPLC can be combined with other means for further analyzing a molecule, for example, to determine its structure. A method for identifying a compound/molecule in an extract or fraction thereof of *H. gentianoides* for decreasing inflammatory responses using mass spectrometry is provided.

The mass spectrometry detection may be conducted with a single quadrupole mass spectrometer, a "tandem-in-space" mass analyzer such as a "triple quadrupole" mass spectrometer and "tandem-in-time" mass analyzer such as a Paul ion trap or Fourier Transform Ion Cyclotron Resonance (FT-ICR). In a single quadrupole mass analyzer, the ionized sample undergoes "upfront" collisionally induced dissociation (CID) between the atmosphere-to-vacuum interface and the mass analyzer. Product ions related to the compounds of interest and unfragmented ions are passed through the mass filter for analysis and detection. Since only a single mass analyzer is used, the selectivity and specificity of this technique may be limited. Using triple quadrupole mass spectrometer, the first mass filter (Q1) selects the molecular ion of interest while the second mass filter selects specified product or fragment ions. Between these stages of mass filtration, the (precursor) molecular ions selected by the first stage undergo collisionally induced dissociation (CID) to produce product or fragment ions. The particular molecular and fragment ions of interest will, of course, vary with the structure of the target of interest. Accordingly, in one aspect, the method of the invention further comprises using tandem mass spectrometry.

Analysis of fraction 2 subjected to HPLC and tandem mass spectrometry revealed the most abundant compounds and their mass to charge ratio (m/z) are found in fraction 2 of the *H. gentianoides* methanol extract, with approximately 90% of the extract mass in fraction 2. The selective fragmentation of the compounds in fraction 2 provided daughter ions yielding structural information. See FIG. 7. Based on the daughter ions observed, the compounds identified are believed to include but are not limited to saroaspidin A, uliginosin B, saroaspidin B or japonicin A, a first sterol, a first acyl-phloroglucinol, a second sterol, uliginosin A, a second acyl-phloroglucinol, and hyperbrasilol C. The compounds' daughter ion mass spectra are shown in FIG. 7. The mass spectra 'fingerprints' are reproducible fragmentation patterns capable of validating the presence of the constituent in this or other extracts.

In one aspect, the method includes detecting a compound of the fraction or extract using tandem mass spectrometry in the negative or positive ionization mode. In one aspect, the method includes detecting or identifying the compound by monitoring daughter ions (m/z) of its molecular ions (m/z). See FIG. 7 and Table 1 as set forth below.

TABLE 1

Mass spectra data of particular molecular ions from MS(2) using the Agilent 1100 ion trap.

| Compound | Molecular Ion | Daughter Ions |
| --- | --- | --- |
| saroaspidin A | m/z 445 | m/z ~ 209, 223, 235 |
| uliginosin B | m/z 497 | m/z ~ 223, 235, 261 |
| saroaspidin B or japonicin A | m/z 459 | m/z ~ 223, 235 |
| a first sterol | m/z 513 | m/z ~ 237, 249, 261, 317 |
| an acyl-phloroglucinol | m/z 499 | m/z ~ 209, 221, 277, 289 |
| a second sterol | m/z 513 | m/z ~ 221, 293, 399, 442 |
| uliginosin A | m/z 499 | m/z ~ 223, 235, 263, 275 |
| a second acyl-phloroglucinol | m/z 513 | m/z ~ 237, 249, 263, 275 |
| hyperbrasilol C | m/z 554 | m/z ~ 263, 277, 289 |

The molecular ions of the compounds may be detected at 445, 497, 459, 513, 499, or 554, respectively. The most abundant daughter-ions of the compounds may be used to monitor the molecular-daughter ion transition for the compounds as shown in FIG. 7 and Table 1.

In one aspect, the method includes detecting and/or measuring the compounds or combinations thereof using tandem mass spectrometry in the negative or positive ionization mode. The molecular ions of each analytes may be determined from spectra by infusing the standard reference compounds. Each molecular ion may be subjected to ion trap fragmentation to obtain their daughter-ion spectra. (FIG. 7). The most abundant product ion is selected and other parameters may be optimized for the multiple reaction monitoring (MRM). Optionally, quantitative analysis of the compounds may be based on the MRM transitions.

In one aspect, the method includes identifying a compound from the fraction or extract using nuclear magnetic resonance spectroscopy (NMR) spectroscopy. One skilled in the art will be familiar with such techniques. NMR studies may be performed by incubating the resolved compound of interest in a solvent suitable for NMR, for example, one that is deuterated. The NMR spectrum may be recorded and analyzed, thereby identifying individual atoms in the compound from the extract or fraction thereof and hence the compound.

In one aspect, the method includes subjecting an extract or fraction to HPLC to resolve at least one compound. As used herein, the term "resolving", "resolved" or variations thereof means sufficiently separating a molecule from other molecules to allow identification of the molecule. For example, the semi-preparative HPLC method described herein may be used to purify enough of the anti-inflammatory or anti-HIV compound(s) for identification, using only one-dimensional separation. If further separation is desired, a different stationary phase for HPLC may be used to purify compounds for identification using, for example, NMR, tandom MS, and FT-IR or any combination thereof. In another aspect, the method includes detecting the separated molecule/compound using tandem mass spectrometry, spectroscopy, for example, NMR spectroscopy, to determine the molecular structure of the compound. The methods of the invention are useful for identifying molecules in an extract or fraction thereof of *H. gentianoides*, including those compounds that have anti-inflammatory activity or anti-HIV activity.

Methods of the present invention may be used to screen for and identify plants that are sources for the compounds described herein, for example, compounds with the same retention time, UV and mass spectra fingerprints, and antiinflammatory or anti-HIV activity as disclosed herein. Preferred plants are those belonging to the *Hypericum* genus or *gentianoides* species. As described above, the method includes introducing an extract or fraction thereof from a plant into a HPLC column and performing tests to evaluate the extract or fractions thereof, for example, liquid chromatography, inflammatory or HIV-inhibition assays, spectroscopy or spectrometry or combination thereof. By comparing the fingerprints and retention times of the compounds in fraction 1 or 2 as disclosed herein that have anti-inflammatory or anti-HIV activity to the fingerprint obtained for an extract, fraction, or compound from another plant, one can identify a plant having the compounds described herein. Using methods of the present invention, one skilled in the art would be able to screen different plants for the presence of compounds in fractions 1 or 2. Identification of those plants, in turn, can be used to as a source for isolating compounds identified by methods of the present invention.

In addition to the extracts, fractions thereof and compounds thereof, the present invention also provides useful therapeutic methods. The methods of the present invention are useful for a variety of applications.

The present invention is directed to the use of plant extracts, fractions thereof, or compounds thereof for use in treatment of inflammation, an inflammation-mediated disease, disorder, or condition, a prostaglandin-mediated disease, disorder, or condition, and/or a COX-mediated disease, disorder, or condition and/or an HIV infection. In one aspect, the methods include administering to a patient in need of such treatment a therapeutically effective amount of an extract, fraction thereof or compound thereof of the present invention. In one aspect, the therapeutically effective amount of an extract, fraction thereof or compound thereof of the present invention is administered as a pharmaceutical composition.

As used herein, "treating" or "treatment" of a state, disorder or condition includes: (1) preventing or delaying the appearance of clinical symptoms of the state, disorder or condition developing in a mammal (subject) that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statically significant or at least perceptible to the patient or to the physician.

As used herein, a "therapeutically effective amount" means the amount of an extract, fraction thereof, or compound thereof that, when administered to a mammal (subject) for treating a disease, disorder or condition, is sufficient to effect such treatment. The "therapeutically effective amount" will vary depending on the extract, fraction, compound, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is the highest safe dose according to sound medical judgment. The extract, fraction thereof, or compound thereof of the invention may be administered in therapeutically effective amounts, alone or in a cocktail with other compounds.

The four classic symptoms of acute inflammation are redness, elevated temperature, swelling, and pain in the affected area, and loss of function of the affected organ. Symptoms and signs of inflammation associated with specific conditions include: rheumatoid arthritis—pain, swelling, warmth and tenderness of the involved joints; generalized and morning stiffness; insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease; autoimmune thyroiditis—weakness, constipation, shortness of breath, puffiness of the face, hands and feet, peripheral edema, bradycardia; multiple sclerosis—spasticity, blurry vision, vertigo, limb weakness, paresthesias; uveoretinitis—decreased night vision, loss of peripheral vision; lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis; scleroderma—Raynaud's disease; swelling of the hands, arms, legs and face; skin thickening; pain, swelling and stiffness of the fingers and knees, gastrointestinal dysfunction, restrictive lung disease; pericarditis; renal failure; other arthritic conditions having an inflammatory component such as rheumatoid spondylitis, osteoarthritis, septic arthritis and polyarthritis—fever, pain, swelling, tenderness; other inflammatory brain disorders, such as meningitis, Alzheimer's disease, AIDS dementia encephalitis—photophobia, cognitive dysfunction, memory loss; other inflammatory eye inflammations, such as retinitis—decreased visual acuity; inflammatory skin disorders, such as, eczema, other dermatites (e.g., atopic, contact), psoriasis, burns induced by UV radiation (sun rays and similar UV sources)—erythema, pain, scaling, swelling, tenderness; inflammatory bowel disease, such as Crohn's disease, ulcerative colitis—pain, diarrhea, constipation, rectal bleeding, fever, arthritis; asthma—shortness of breath, wheezing; other allergy disorders, such as allergic rhinitis—sneezing, itching, runny nose conditions associated with acute trauma such as cerebral injury following stroke—sensory loss, motor loss, cognitive loss; heart tissue injury due to myocardial ischemia—pain, shortness of breath; lung injury such as that which occurs in adult respiratory distress syndrome—shortness of breath, hyperventilation, decreased oxygenation, pulmonary infiltrates; inflammation accompanying infection, such as sepsis, septic shock, toxic shock syndrome—fever, respiratory failure, tachycardia, hypotension, leukocytosis; other inflammatory conditions associated with particular organs or tissues, such as nephritis (e.g., glomerulonephritis)-oliguria, abnormal urinalysis; inflamed appendix—fever, pain, tenderness, leukocytosis; gout—pain, tenderness, swelling and erythema of the involved joint, elevated serum and/or urinary uric acid; inflamed gall bladder—abdominal pain and tenderness, fever, nausea, leukocytosis; chronic obstructive pulmonary disease—shortness of breath, wheezing; congestive heart failure—shortness of breath, rales, peripheral edema; Type II diabetes—end organ complications including cardiovascular, ocular, renal, and peripheral vascular disease lung fibrosis—hyperventilation, shortness of breath, decreased oxygenation; vascular disease, such as atherosclerosis and restenosis—pain, loss of sensation, diminished pulses, loss of function and alloimmunity leading to transplant rejection—pain, tenderness, fever.

The term "treating cyclooxygenase mediated disease, disorder or condition" means treating a disease, disorder or condition that is advantageously treated or prevented by inhibiting the cyclooxygenase enzyme. The term includes the relief of pain, fever and inflammation of a variety of conditions including rheumatic fever, symptoms associated with influenza or other viral infections, common cold, low back pain, neck pain, dysmenorrhea, headache, migraine, toothache, sprains and strains, myositis, neuralgia, synovitis, arthritis, including rheumatoid arthritis, degenerative joint diseases (osteoarthritis), gout, ankylosing spondylitis, bursitis, burns, injuries, and pain and inflammation following surgical procedures. In addition, such a compound may inhibit cellular neoplastic transformations and metastatic tumor growth and hence can be used in the treatment and/or prevention of cancer. In addition, such a compound may inhibit the onset or progression of Alzheimer's disease or cognitive impairment. The term also includes the treatment and/or prevention of cyclooxygenase-mediated proliferative disorders such as may occur in diabetic retinopathy and tumor angiogenesis. The term "treating" encompasses not only treating a patient to relieve the patient of the signs and symptoms of the disease or condition but also prophylactically treating an asymptomatic patient to prevent the onset or progression of the disease or condition.

The extracts, fractions, and compounds of the invention may be administered to subjects (animals, most particularly mammals including humans) afflicted with any disease, disorder or condition characterized by undesirable prostaglandin production resulting from cyclooxygenase activity, particularly COX-2 activity. In particular, the extracts, fractions, and compounds of the invention are believed useful in treating inflammation and inflammation-related disorders, by administering to a subject having or susceptible to such inflammation or inflammation-related disorder and effective amount of an extract, fraction thereof or compound thereof according to invention. Inflammation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, low back and neck pain, dysmenorrhea, headache, toothache, sprains and strains, myositis, neuralgia, synovitis, gout and ankylosing spondylitis, bursitis, and following surgical and dental procedures. The extract, fraction thereof or compound thereof of the invention are believed useful as analgesics for treating or alleviating all forms of pain. The compounds are believed useful in the treatment of other disorders including asthma, bronchitis, tendonitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflammation in such diseases as vascular diseases, migraine headaches, periarteritis nodosa, thyroiditis, aplastic anemia, Hodgkin's disease, sclerodoma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The an extract, fraction thereof or compound thereof of the invention are believed useful as antipyretics for the treatment of fever.

In addition, an extract, fraction thereof or compound thereof of the invention may inhibit cellular neoplastic transformations and metastatic tumor growth and hence can be used in the treatment of cancer. In particular, the present invention provides a method for treating or preventing a neoplasia that produces a prostaglandin in a subject in need of such treatment or prevention, the method comprises treating the subject with a therapeutically effective amount of an extract, fraction thereof or compound thereof. The term "neoplasia" includes neoplasias that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The compounds may be used to inhibit the growth or an established neoplasm, i.e., to induce regression, or to prevent or delay the onset of the neoplasm.

According to U.S. Pat. No. 5,972,986, neoplasias that produce prostaglandins, and which are therefore believed treatable with the compounds of the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The extract, fraction thereof or compound thereof of the invention may also be useful in the treatment of angiogenesis-mediated disorders. Thus, a method for treating, inhibiting or delaying the onset of an angiogenesis-mediated disorder in a subject is provided comprising administering to a subject in need of such treatment an effective amount of an extract, fraction thereof or compound thereof according to the present invention. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The extract, fraction thereof or compound thereof of the invention may also be useful in the treatment of Alzheimer's Disease, presenile dementia, stroke and cerebral ischemia. Thus, a method for treating, inhibiting or delaying the onset of Alzheimer's Disease, presenile dementia, stroke or cerebral ischemia in a subject is provided comprising administering to a subject in need of such treatment an effective amount of an extract, fraction thereof or compound thereof according to the present invention. U.S. Pat. Nos. 6,486,194, 5,932,598 and 6,432,999, the entire disclosures of which are incorporated herein by reference, disclose that neurodegenerative diseases, including Alzheimer's disease, stroke and cerebral ischemia may be treated by administering non-steroidal cyclooxygenase-2 inhibitors.

The extract, fraction thereof or compound thereof of the invention may also be useful in the treatment of tissue ischemia, such as ischemia of the myocardium. Thus, a method for treating, inhibiting or delaying the onset of tissue ischemia, particularly stroke (CNS ischemia), and ischemia of the myocardium in a subject is provided comprising administering to a subject in need of such treatment an effective amount of an extract, fraction thereof or compound thereof according to the present invention. U.S. Pat. Nos. 6,451,794, 6,432,999 and 5,932,598, the entire disclosures of which are incorporated herein by reference, disclose that tissue damage associated with tissue ischemia, such as ischemia of the myocardium, may be treated by administration of an extract, fraction thereof or compound thereof that are inhibitors or selective inhibitors of COX-2.

A plant extract, fraction thereof or compound thereof identified and isolated by a method of the present invention, may be utilized as an anti-inflammatory or anti-HIV drug.

In one embodiment, in addition to extracts, fractions thereof or compounds thereof or compounds isolated therefrom, the compositions of the present invention may include a pharmaceutically acceptable carrier.

In order to facilitate administration, the extracts, fractions thereof and compounds thereof may be mixed with any of a variety of pharmaceutically acceptable carriers for administration. "Pharmaceutically acceptable" as used herein means that the extract, fraction thereof, or compound thereof or composition is suitable for administration to a subject to achieve the treatments described herein, without unduly deleterious side effects in light of the severity of the disease and necessity of the treatment. The carrier may be a solid or a liquid, or both, and is preferably formulated with the compound as a unit-dose formulation, for example, a tablet, which may contain from 0.5% to 95% by weight of the active compound. One or more of each of the anti-inflammatory or anti-HIV extracts, fractions thereof or compounds thereof of the present invention may be incorporated in the formulations of the invention, which may be prepared by any of the well known techniques of pharmacy consisting essentially of admixing the components, optionally including one or more accessory ingredients. In one embodiment, the extracts, fractions, and compounds of this invention may be administered in conjunction with other medicaments known to those of skill in the art.

Other compatible pharmaceutical additives and actives may be included in the pharmaceutically acceptable carrier for use in the compositions of the present invention.

One embodiment includes administering a composition for the treatment of inflammation, a prostaglandin-mediated or cyclooxygenase-mediated disease, disorder or condition, or an HIV-infection including an extract, fraction thereof or compound thereof and a carrier. In one aspect, the prostaglandin-mediated disease, disorder or condition is a PGE2-mediated disease, disorder or condition. In another aspect, the cyclooxygenase-mediated disease, disorder or condition is a COX2-mediated disease, disorder or condition. As used herein, a subject may be a human, non-human primate, cow, horse, pig, sheep, goat, dog, cat, or rodent and the like.

Dose ranges can be adjusted as necessary for the treatment of individual patients and according to the specific condition treated. Any of a number of suitable pharmaceutical formulations may be utilized as a vehicle for the administration of the compositions of the present invention and maybe a variety of administration routes are available. The particular mode selected will depend of course, upon the particular formulation selected, the severity of the disease, disorder, or condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes and the like. Accordingly, the formulations of the invention include those suitable for oral, rectal, topical, buccal, parenteral (e.g., subcutaneous, intramuscular, intradermal, inhalational or intravenous) and transdermal administration, although the most suitable route in any given case will depend on the nature and severity of the condition being treated and on the nature of the particular active product used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal administration include lozenges comprising the active compound in a flavored base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by admixing the compound with water or a glycine buffer and rendering the resulting solution sterile and isotonic with the blood. Alternately, the extracts, fractions thereof or compounds thereof can be added to a parenteral lipid solution.

Formulations suitable for rectal administration are preferably presented as unit dose suppositories. These may be prepared by admixing the active compound with one or more conventional solid carriers, for example, cocoa butter, and then shaping the resulting mixture.

Formulations of the inventive mixtures are particularly suitable for topical application to the skin and preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current to "inject" electrically charged ions into the skin) through the skin. For this, the dosage form typically takes the form of an optionally buffered aqueous solution of the active compound. Suitable formulations comprise citrate or bis/tris buffer (pH 6) or ethanol/water and contain from 0.01 to 0.2M active ingredient.

Mammals may be treated using the methods of the present invention and are typically human subjects although the methods of the present invention may be useful for veterinary purposes with other subjects, particularly mammalian subjects including, but not limited to, horses, cows, dogs, rabbits, fowl, sheep, and the like. As noted above, the present invention provides pharmaceutical formulations comprising extracts, fractions thereof or compounds thereof or combinations thereof of the present invention, or pharmaceutically acceptable salts thereof, in pharmaceutically acceptable carriers for any suitable route of administration, including but not limited to oral, rectal, topical, buccal, parenteral, intramuscular, intradermal, intravenous, and transdermal administration.

The therapeutically effective dosage of any specific compound will vary somewhat from compound to compound, patient to patient, and will depend upon the condition of the patient and the route of delivery. As a general proposition, a dosage from about 0.01 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight or volume of the anti-inflammatory extracts, fractions thereof or compounds thereof of the present invention, including the cases where a salt is employed.

The present invention also provides medical foods comprising anti-inflammatory or anti-HIV extracts, fractions thereof or compounds thereof of the present invention or any combination thereof, the medical food being compounded for the amelioration of a disease, disorder or condition associated with or caused by inflammation or HIV.

This invention can be better understood by reference to the following non-limiting examples. It will be appreciated by those skilled in the art that other embodiments of the invention may be practiced without departing from the spirit and the scope of the invention as herein disclosed and claimed.

Example 1

Extracts

Plant material was acquired through the USDA North Central Regional Plant Introduction Station in Ames, Iowa. A voucher sample was collected and the accession is listed in the GRIN database. The whole upper aerial portion of the mature flowering plant was used.

Dry plants were ground in liquid nitrogen and immersed in methanol. The methanol/tissue was sonicated three times with a probe sonicator for 30 seconds and then repeated twice more. Samples were then centrifuged and the supernatant decanted. The sample was then filtered through 0.45 micron nylon syringe filters. Solvent was evaporated under nitrogen gas at 40° C. to prevent oxidation. The dried extract was weighed and then dissolved in cell culture grade DMSO.

HPLC

A Beckman Coulter HPLC with a Detector 160 PDA detector was used for initial chemical profiling. A Synergi Max-RP 150×4.6 mm column (Phenomenex Torrance, Calif. 90501) was used for analytical separation. For the mobile phase an acetonitrile/methanol 9:1 v/v (solvent B) and 10 mM ammonium acetate (solvent A) gradient was used. The gradient consisted of 87A/13B in 10 minutes to 83A/17B, then to 100% B in 25 min and held for 5 min, at 40° C. The flow rate was 1.0 mL/min (Ganzera M., J. Z. I. A. K. (2002), "*Hypericum perforatum*-Chemical profiling and quantitative results of St. John's Wort products by an improved high-performance liquid chromatography method," *Journal of Pharmaceutical Sciences* 91(3):623-630).

LC-MS

The extracts were also analyzed with an Agilent Technologies Ion Trap 1100 LC-ESI-MS. A Synergi Max-RP 150×4.6 mm column (Phenomenex Torrance, Calif. 90501) was used for analytical separation. For the mobile phase an acetonitrile/methanol 9:1 v/v (solvent B) and 10 mM ammonium acetate (solvent A) gradient was used. The gradient was from 85A/15B in 10 min to 80A/20B, then to 100% B in 25 minutes and held at 100% B for 5 min, at 40° C. The flow rate was 0.75 mL/min (Ganzera M., J. Z. I. A. K. (2002)).

Example 2

Semi-Preparative HPLC

A Synergi Max-RP 250×10 mm column (Phenomenex Torrance, Calif. 90501) was chosen since it matches the stationary phase of the analytical method. For the mobile phase an acetonitrile/methanol 9:1 v/v (solvent B) and 10 mM ammonium acetate (solvent A) gradient elution was used; 13-15% B in 10 minutes, 15-100% B in 30 minutes, 100% B for 5 minutes, at 40° C. The slow rise from 13% to 15% over 10 min optimized the separation of more polar phenylpropanoids from later eluting flavonoids. While a range of flow rates from 3-5 mL/min were tested, a flow rate of 4.6 mL/min optimized separation of compounds, and matched retention times with the analytical method within 3 min or less.

Cell Culture

RAW264.7 macrophages were purchased from the American Type Culture Collections (ATCC; Manassas, Va.) and cultured in high glucose Dulbecco's Modified Eagle's medium (4500 mg/L D-glucose) (Invitrogen, Carlsbad, Calif.) and supplemented with 100 UI/ml penicillin/streptomycin (Invitrogen, Carlsbad, Calif.) and 10% Fetal Bovine Serum (FBS) (Invitrogen, Carlsbad, Calif.). Cells were maintained in a 5% $CO_2$ incubator with 70% humidity for 37° C. until 70% confluent in 75 $cm^2$ flasks.

Cell Treatments

Cells were plated at a density of 1.0×10$^5$ cells/well in 24-well cell culture plates and allowed to attach overnight. Cells were incubated with or without 1 μg/ml lipopolysaccharide (LPS) (*E. coli* 02B:B6) (Sigma, St. Louis, Mo.) and solvent alone, dimethylsulfoxide (DMSO) (Sigma, St. Louis, Mo.), or *H. gentianoides* extract or fraction simultaneously for 8 hours. Cell supernatants were collected on ice, and stored in a −70° C. freezer for use in the PGE2 assay. DMSO concentration did not exceed 0.1% of the media, an amount determined by preliminary testing. Four controls were included in each treatment: media alone, media and DMSO, media and LPS, and media and LPS and DMSO. In addition, 10 μM quercetin was used as a positive control. Since *H. perforatum* contains light-activated compounds, the *H. gentianoides* extract was tested in both light-activated and dark conditions initially to determine if the activity was dependent on light activation. There was no significant difference between the light-activated and dark treatment conditions and therefore the rest of the treatments were performed in ambient light.

PGE2 Assay

The supernatant samples were assayed with a Prostaglandin $E_2$ EIA kit (GE Biosciences, Piscataway, N.J.) according to manufacturer's instructions. Supernatants were diluted 1:15 in water to ensure the concentration of PGE2 present within the samples were within the linear range of the standard curve for the assay.

Cytotoxicity Assay

CellTiter96® Aqueous One Solution cell proliferation assay (Promega Corporation, Madison, Wis.) was used as previously described in Schmitt et al. with an 8-hour treatment incubation instead of 24-hour treatment incubation to parallel the anti-inflammatory studies (Schmitt, L. A., et al., (2006)). Following the 8 hour incubation, treatment solutions were removed and fresh media and Celltiter96® dye were added for 3 hours and 15 minutes (Schmitt, L. A., et al., (2006)). The metabolized dye solutions were transferred to 96-well plates for absorbance measurement at 490 nm. The number of viable cells for each treatment was compared to the media+DMSO solvent control. Treatment with 20 µM hypericin was used as a positive control.

Statistical Analysis

Data is shown as mean percent reduction in LPS-induced PGE2 levels±the standard error as compared to the media+LPS+DMSO control. Statistical significance was determined by an F-protected two-way ANOVA followed by a Tukey-Kramer test for multiple comparisons (Snedecor, G. W., Cochran, W. G., Eds. (1989). *Statistical Methods*, $8^{th}$ ed. University Press: Ames, Iowa). For cytotoxicity, data are represented as mean % cytotoxicity±standard error as compared to the media+DMSO control. Statistical significance was determined by an F-protected two-way ANOVA followed by a Dunnett-Hsu test for multiple comparisons (Dunnett C. W. (1955). "A multiple comparison procedure for comparing several treatments with a control." *Journal of the American Statistical Association.* 50:1096-1121). P-values less than 0.05 were considered statistically significant.

Example 3

To maximize the discovery of new potentially bioactive metabolites, *Hypericum* extraction methods were developed to maximize the preservation of unstable compounds while optimizing the extraction efficiency of a broad range of compounds. The extraction protocol was developed to be non-destructive, meaning it would not degrade easily oxidized compounds such as prenylated acylphloroglucinols. Hence there was no addition of heat, with all of the procedure occurring at or below room temperature. Methods such as soxhlet extraction are efficient; however, it can destroy thermally unstable compounds (Liu, F. F., C. Y. W. Ang, et al. (2000), "Optimization of Extraction Conditions for Active Components in *H. perforatum* Using Response Surface Methodology," *J. Agric. Food Chem.* 48(8): 3364-3371). Since *Hypericum* species are known to contain unstable active compounds, namely phloroglucinols, liquid nitrogen grinding and sonication techniques were used to avoid altering the compounds. Also, solvent selection was important for concentrating the extract later. Extraction using an ethanol-water mixture was avoided, although it efficiently extracts metabolites from *Hypericum*, because high temperatures or long periods of time in a lyophilizer are required to remove water when the sample was being concentrated. Methanol was a more logical choice since the organic extract could be evaporated easily and quickly, while it effectively extracted a broad range of compounds similar to a 70% ethanol solvent. In accordance with Crockett et al. (Crockett Sara L., B. S. I. A. K. (2005), "Phytochemical profiling of new and old world *Hypericum* (St. John's Wort) species," *Phytochemical Analysis* 16(6): 479-485), but using a different accession of *H. gentianoides*, chlorogenic acid, hyperoside, and isoquercitrin with standards by HPLC (FIG. 1A) were identified. Furthermore, HPLC separation, using the methanol low temperature extraction method developed and described herein, revealed an abundance of unknown metabolites (FIG. 1B). Four grams of dry plant material yielded approximately one gram of extracted metabolites.

Unlike many other species in the *Hypericum* genus, *H. gentianoides* does not contain hypericin or hyperforin, two heavily studied bioactive compounds from St. John's Wort. *H. gentianoides* has a very different chemical profile compared to the heavily studied *H. perforatum*. HPLC analysis revealed numerous novel compounds. The ultraviolet (UV) radiation absorption spectra of the HPLC UV absorbing metabolites show that this species appears to have a large number of a related class of compounds, with a retention time from about 30 to about 45 minutes. There are at least nine constituents with the characteristic UV absorption maxima at 220, 300, and 350 nm; or at 226, 287, and 357 nm.

Figure 2:
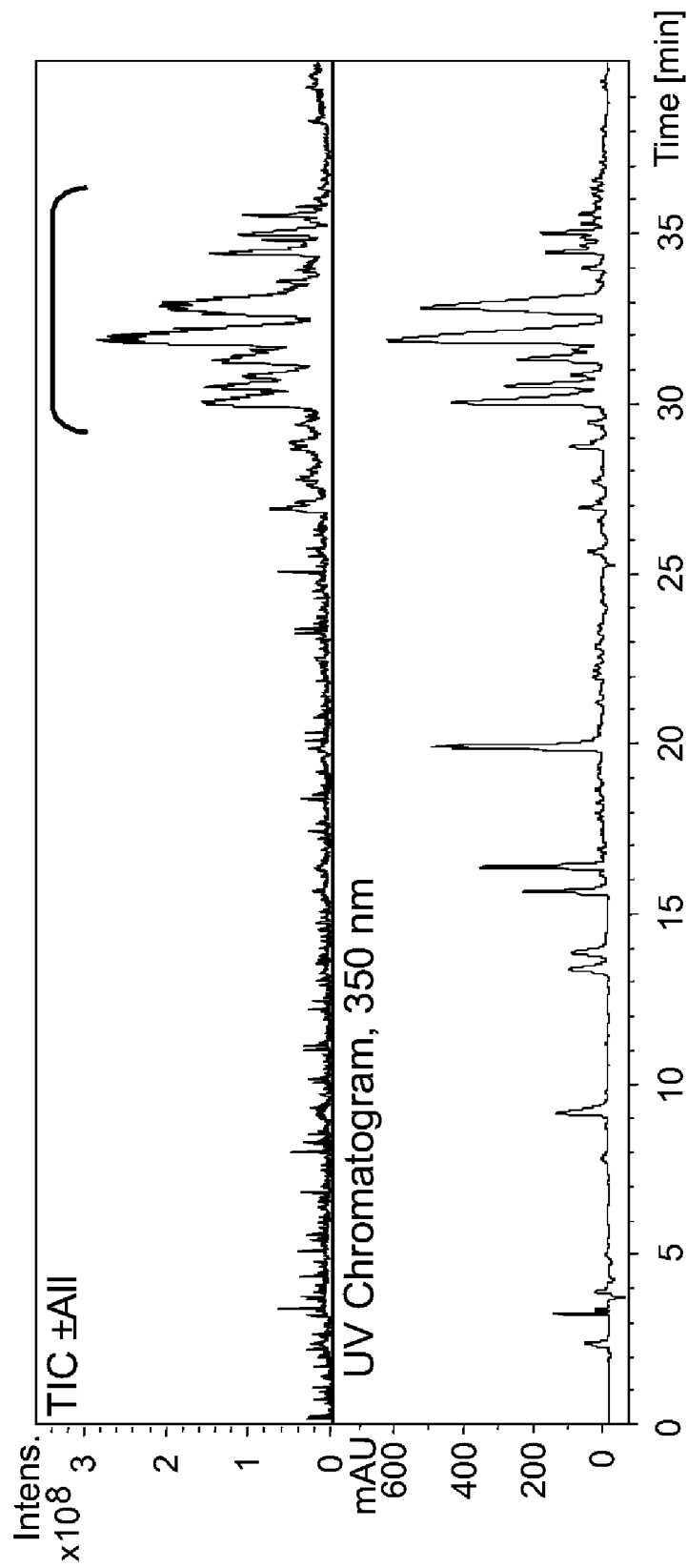
FIG. 2. The unknown class of lipophilic compounds from *H. gentianoides* comprises a large amount of the extract's mass. The total ion chromatograph (TIC) from the liquid chromatography-electrospray ionization-mass spectrum analysis, with coupled UV absorption data, for *H. gentianoides* is shown above. The unknown compounds highlighted with the blue bar comprise most of the sample's mass. The high abundance is crucial for the feasible purification of enough material for bioactivity-guided fractionation.

LC-ESI-MS was used to provide more physical information about these compounds. The total ion chromatograph shows that the majority of the mass in the extract consists of the unknowns with a retention time between about 28 to 38 minutes, and preferably from about 30 and 35 minutes (FIG. 2).

Figure 3:
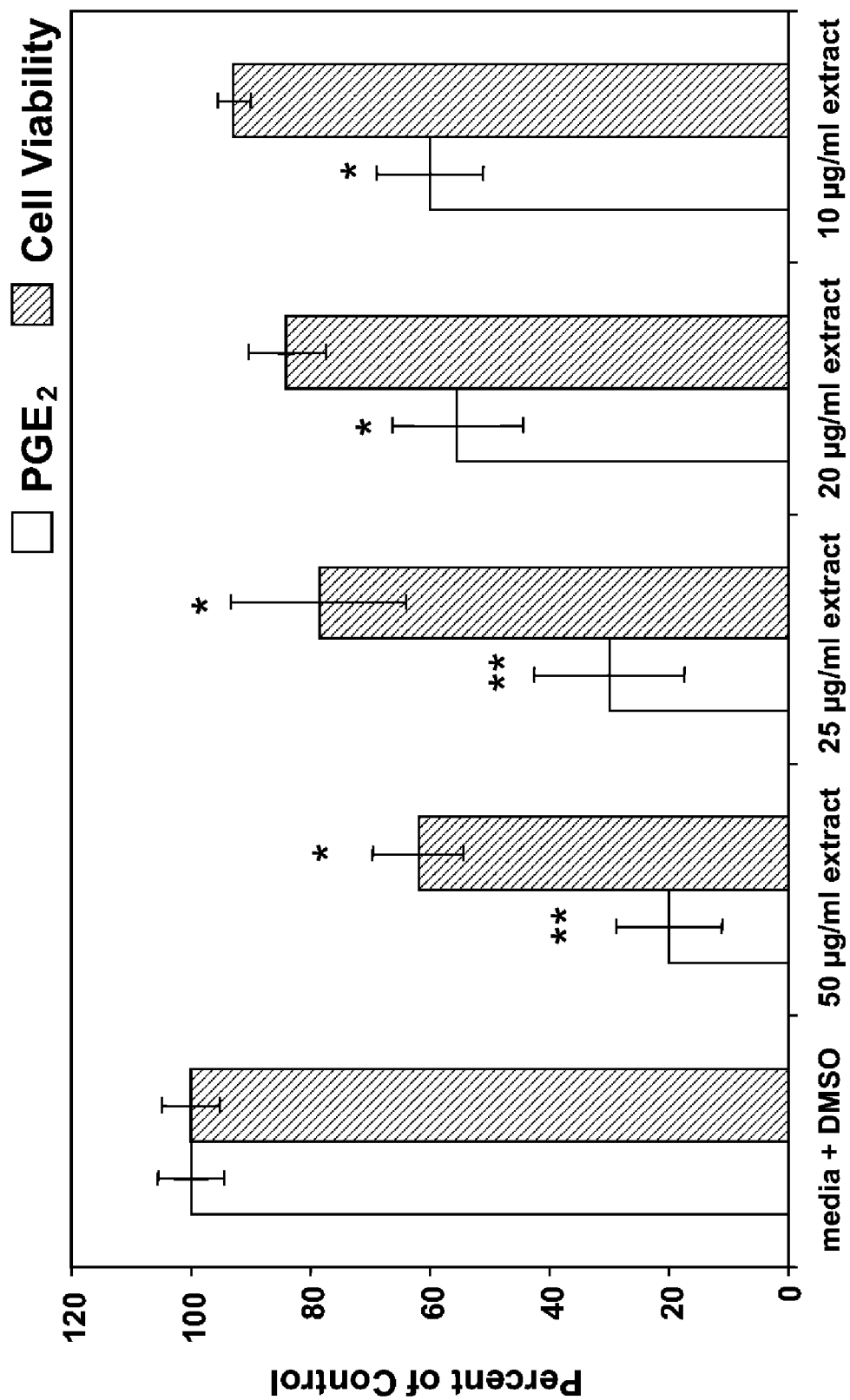
FIG. 3. Lipopolysaccharide (LPS)-induced RAW 264.7 macrophages treated with the *H. gentianoides* methanol extract had significantly reduced prostaglandin E2 concentrations, compared to the non-treated macrophages. Decreased percent of control for PGE2 treated cells indicates increased anti-inflammatory activity. This reduction was concentration dependent. Anti-inflammatory activity (mean percent of media+DMSO+LPS PGE2 level±standard error) and cytotoxicity (mean percent of media+DMSO cell viability±standard error) of *H. gentianoides* extracts (n=6 for each). The concentration tested in μg/ml represents the final concentration of the extract in the media. Addition of LPS to the culture media+DMSO control increased the level of PGE2 11 fold over media+DMSO control alone (0.12±0.02 ng/ml for media+DMSO, 1.4±0.1 ng/ml for media+DMSO+LPS). Extracts in the culture media without LPS did not affect the concentration of PGE2 as compared to the media+DMSO control. * p-value less than 0.05 as compared to control. ** p-value less than 0.0001 as compared to control.

To assess biological activity in mammals RAW264.7 macrophage model system was used, in which LPS is used to induce an anti-inflammatory response (Schmitt, L. A., Liu, Y., Murphy, P. A., Birt, D. F. (2006), Evaluation of the light-sensitive cytotoxicity of *H. perforatum* extracts, fractions, and pure compounds, *J. Agric Food Chem.* 54:2681-2890). The ability of *H. gentianoides* extracts to reduce the inflammatory response was assessed by quantifying PGE2 production in LPS-induced macrophages. Initial assays indicated a significant reduction of PGE2, compared to the controls. To establish the concentration of extract needed to induce bioactivity, macrophages were treated with various concentrations of plant extract from 10-50 µg/mL. This revealed a dose response, with decreasing PGE2 concentrations the higher the concentration of the extract applied (FIG. 3). Studies performed in light and dark conditions confirmed that cytotoxicity was not light-induced. This is important since it validates that there are no dianthrones or other light-activated compounds in the *H. gentianoides* extract.

Figure 4:
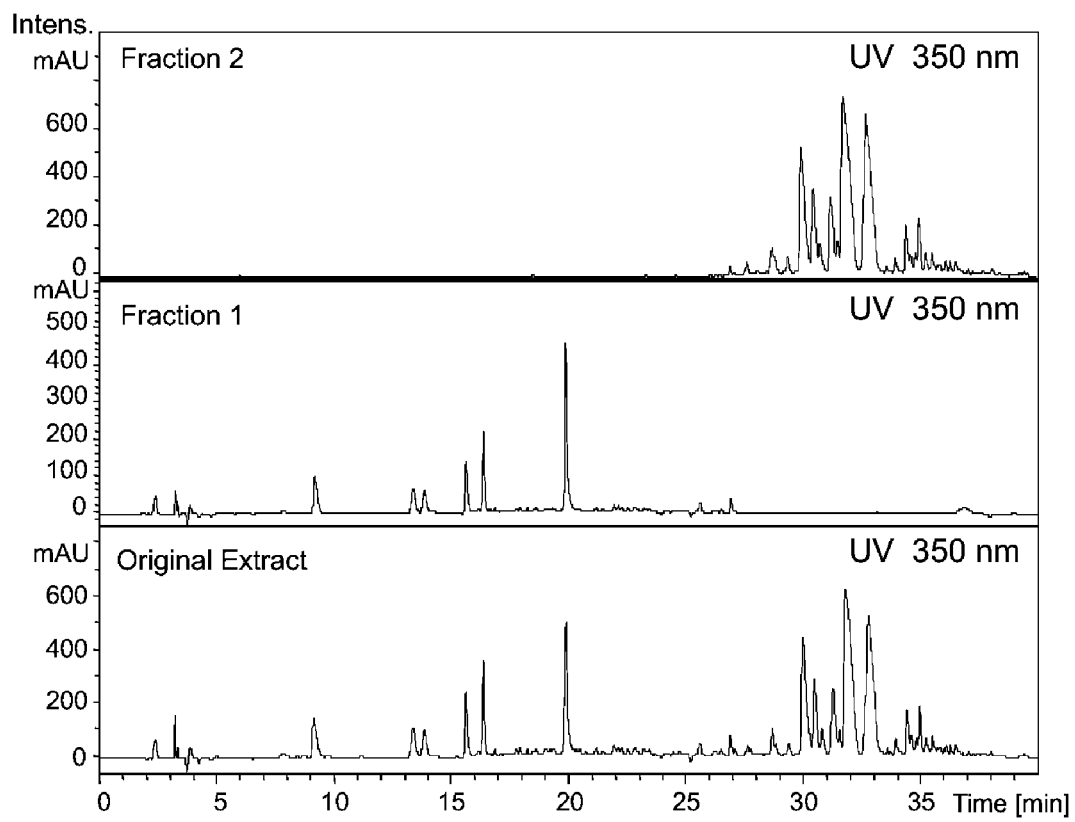
FIG. 4. Analysis of the of the semi-preparative HPLC separation by analytical LC-MS-UV. The initial separation of the methanol extract divided the more lipophilic constituents (Fraction 2) from more polar constituents for instance flavonoids such as quercetin at retention time 20 min (Fraction 1). Semi-preparative HPLC was used for bioactivity guided fractionation since it is very reproducible and requires only gram quantities of starting material. This is due to the fact that further separation can reoccur starting with the original material again, as opposed to continuously diluting the previous bioactive fraction(s). All subsequent fractions were made using this method. A Synergi Max-RP 250×10 mm column (Phenomenex Torrance, Calif. 90501) was chosen since it matches the stationary phase of the analytical method, which provides the same elution order of compounds. While a range of flow rates from 3-5 mL/min were tested, a flow rate of 4.6 mL/min optimized separation of compounds, and matched retention times with the analytical method within 3 min or less.

To determine which compound(s) are responsible for the bioactivity, a semi-preparative HPLC method was developed to fractionate the *H. gentianoides* extract. The optimized protocol achieves good separation, has a high loading capacity, the same compound elution order as the analytical separation data, and allows for the isolation of enough fraction material for biological testing in a reasonable amount of time. Analytical HPLC separation shows the composition of the extract, and that of fractions 1 and 2 (FIG. 4). Fraction 2 includes compounds having an UV absorption maxima fingerprint of 230/300/350 nm.

LPS-induced RAW 264.7 macrophages were treated with the two HPLC fractions or the original extract. In the LPS-induced cells, Fraction 2 significantly reduced the PGE2 concentration at every dose tested ranging from 30 µg/mL to 10 µg/mL, while Fraction 1 did not reduce the PGE2 concentration at similar doses. This indicated that the active constituents are in Fraction 2 (FIG. 5). Further testing revealed that Fraction 2 significantly reduces PGE2 concentrations even as low as 1 µg/mL (FIG. 6). To determine what impact the fraction had on macrophages cytotoxicity testing was performed. At doses of 30 µg/mL macrophage viability was 70%, at 10 µg/mL it was 78%, while at 5 µg/mL and less macrophage viability was 100%, with no significant cytotoxicity to the macrophages; after the eight-hour treatment period (FIG. 6).

Example 4

In conclusion, an extraction method for *H. gentianoides* that preserved unstable compounds was developed, and a fractionation method for bioactivity-guided separation of the extract. Using these procedures, it was determined that extracts from *H. gentianoides* reduce the synthesis of the pro-inflammatory compound PGE2 in LPS-induced RAW 264.7 macrophages, and that doses of Fraction 2 in FIG. 4 significantly reduce PGE2 concentrations at any dose, and doses of 1 µg/mL showed no cytotoxicity. The dosage of 1 µg/mL was the lowest dosage tested; however, it is understood that lower dosages may possess activity and could readily be tested for activity. This bioactivity is present in more than one accession of *H. gentianoides* (data not shown), confirming that the bioactivity is reproducible independent of not only the sample, but also is characteristic of a number of populations of this species.

The distinct morphology, potent bioactivity, and unusual chemical profile of *H. gentianoides*, compared to other *Hypericum* species from Eurasia and North America, justifies further investigation. A study comparing the chemical profiles of species in the Section Brathys, to which *H. gentianoides* belongs, and perhaps species in Section Trigynobrathys would enrich the understanding of why *H. gentianoides* is so different from other North American species. One possibility is that this species is more closely related to South American species in the *Hypericum* genus than to the North American species. Phylogenetic studies would help to distinguish among these possible scenarios.

The characteristic UV absorption fingerprints of at least 9 HPLC peaks in the bioactive fraction indicate that the predominant constituents may be biosynthetically related. The UV absorption maxima and the retention time of these unknowns are consistent with acyl-phloroglucinols. Frequently, individual *Hypericum* species contain unique compounds specific to that species only. It is postulated that at least some of the bioactive anti-inflammatory compound(s) from *H. gentianoides* have not yet been identified. The identification of the bioactive unknown(s) contained within the active Fraction 2 is in progress. Further fractionation of the extract is required to identify the bioactive compounds. The identification will be possible with further bioactivity assays, LC-MS, and NMR spectroscopy studies. Furthermore, the reduction of PGE2 indicates reduced cyclo-oxygenase activity since PGE2 is the product of this class of enzyme, but the mechanism by which this regulation is occurring is unknown.

Example 5

Prophetic Examples

Tandem Mass Spectrometry

Tandem mass spectrometry with a Applied Biosystems LC/MS-Q Star may be used to identify the exact mass of the anti-inflammatory compounds found in *H. gentianoides*. This will give empirical chemical formula information useful for verifying the proposed structures of the compounds. The Agilent Ion Trap 1100 will also be used to provide structural information of anti-inflammatory compounds based on daughter ion fragmentation patterns.

NMR

Various one-dimension and two-dimensional NMR experiments will be used to identify the chemical structure of the anti-inflammatory compounds. These may include HSQC, proton-proton coupling, carbon-13 NMR, and distortionless enhancement by polarization transfer (DEPT) carbon-13 NMR. The instrument used is a Bruker wide bore 600 MHz spectrometer. Shigemi NMR tubes will be used to maximize the concentration of the isolated compound to increase sensitivity.

HPLC Conditions to Resolve Individual Compounds

Current methods provide crude purification for individual compounds of interest. Certain compounds may require additional separation using a different stationary phase, such as a C18 reverse-phase column or ion-exchange column.

Fourier Transform Infrared Spectroscopy

FT-IR may be used to identify various functional groups of the anti-inflammatory compound(s).

Example 6

HIV Inhibition

Plant Tissue Extracts

Plant material was acquired through the USDA North Central Regional Plant Introduction Station in Ames, Iowa. A voucher sample was collected and the accession is listed in the GRIN database.

Dry plants where ground in liquid nitrogen and immersed in methanol. The methanol/tissue was sonicated with a probe sonicator for 30 seconds and then repeated twice more. Samples where then centrifuged and the supernatant decanted. This supernatant was filtered through 0.45 micron nylon syringe filters. Solvent was evaporated under nitrogen gas to prevent oxidation. The dried extract was weighed and then dissolved in cell culture grade DMSO for testing.

HPLC

A Beckman Coulter HPLC with a Detector 160 PDA detector was used for initial chemical profiling. A Synergi Max-RP 150×4.6 mm column (Phenomenex Torrance, Calif. 90501) was used for analytical separation. For the mobile phase an ACN/MtOH 9:1 v/v and 0.1% acetic acid gradient was used. The gradient consisted of 87A/13B in 10 minutes to 83A/17B, then to 100% B in 25 minutes and held for 5 minutes, at 40° C. The flow rate was 1.0 mL/min (Ganzera 2002).

LC-MS

The extract was also analyzed with an Agilent Technologies Ion Trap 1100 LC-UV-MS. A Synergi Max-RP 150×4.6 mm column (Phenomenex Torrance, Calif. 90501) was used for analytical separation. For the mobile phase an ACN/MtOH 9:1 v/v and 10 mM ammonium acetate gradient was used. The gradient consisted of 85A/15B in 10 minutes to 80A/20B, then to 100% B in 25 minutes and held for 5 minutes, at 40° C. The flow rate was 0.75 mL/min (Ganzera 2002).

Semi-Preparative HPLC

A Synergi Max-RP 250×10 mm column (Phenomenex Torrance, Calif. 90501) was used for semi preparative HPLC to fraction the *H. gentianoides* extract for further bioactivity testing. For the mobile phase an ACN/MtOH 9:1 v/v and 0.1% acetic acid gradient elution was used; 13-15% B in 10 minutes, 15-100% B in 30 minutes, 100% B for 5 minutes, at 40° C. The flow rate was 4.6 mL/min.

HIV Infections and Cell Viability Assays

Viral stocks of the infectious molecular clone, pNL4-3, were used for all of our studies (1). To generate stocks, 15 cm plates of 293T were transfected with pNL4-3 using calcium phosphate precipitation. Supernatant was collected at 24, 48 and 72 h, post transfection. Viral titers were determined as previously described (5) using HeLa 37 cells that express CD4 and both chemokine co-receptors CCR5 and CXCR4 (4).

Single hit assays were performed as previously described (5). Hela37 cells were distributed in a 48 well plate (20,000 cells/well) 24 hours prior infection. The media (DMEM supplemented with 10% FCS and Penicillin/Streptomycin) was removed and replaced with fresh media containing HIV with and without serial dilutions of *H. gentianoides* extract. Between 0.0025 and 0.005 multiplicity of infection (MOI) of virus was added to each well. DMSO concentrations were adjusted so that all wells contained equivalent concentrations and DMSO concentrations were never greater than 1%. All treatments were performed in triplicate. Virus and cells were incubated at 37° C. for 40 hours. At the completion of the assay, cells were fixed 10 min with 75% acetone/25% water solution and then immunostained utilizing human anti-HIV antisera (kind gift of Dr. J. Stapleton, Univ. Iowa), followed by HRP-conjugated goat anti-human IgG. AEC was utilized as the HRP substrate. HIV antigen-positive cells were counted and recorded. Wells treated with extracts were compared to control, infected wells. Data are presented as the number of HIV positive cells in the presence of extract/the number of HIV positive cells in the absence of extract.

Cell viability studies were performed using ATPLite (Packard Instruments) as previously described (3). The ATPLite kit measures the level of ATP present in the cell population and is a reliable estimate of cell numbers present. HeLa 37 cells were treated in triplicate with serial dilutions of extracts or equivalent concentrations of the vehicle, DMSO. Cultures were maintained for 40 h and harvested for analysis in parallel with the HIV infection plates. Plates were rinsed once with PBS and lysed per manufacturer's instructions. Substrate was added and the plates were read in a microtiter plate reader at 430 nm. Data are presented as the ATP activity present in the well in the presence of extract/the ATP activity present in the well in the absence of extract.

Figure 8:
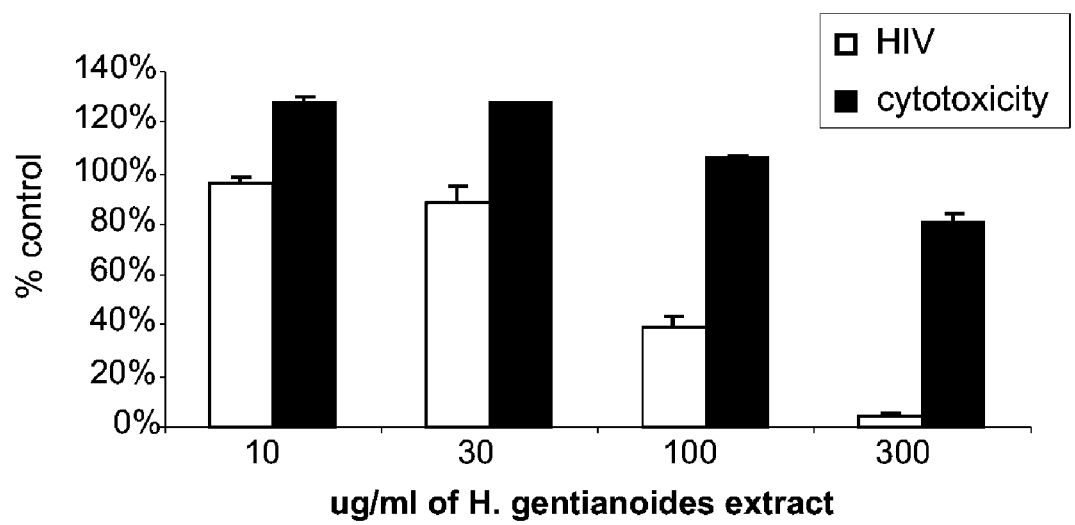
FIG. 8. Testing of the *H. gentianoides* alcohol extract revealed that it was capable of reducing HIV infection in vitro, while cytotoxicity at the same concentration was comparatively low.

To test what sort of unique properties these and other novel compounds may have compared to St. John's Wort, an in vitro HIV inhibition assay was performed. The results indicated there was activity, and that the relative amount of cytotoxicity was low per concentration (FIG. 8). The dose dependent response indicates that there appears to be an optimal concentration with maximum effectiveness and minimal cytotoxicity. Testing of the two fractions indicates there is no inhibition of HIV infection by fraction 1.

The UV absorption spectra of the unknown peaks with a retention time between 29-34 minutes in FIG. 1 suggests the unknowns are benzophenones. However, further identification studies are currently under way to elucidate the structures of the major unknown compounds. Some of these peaks are a significant portion of the total extract's mass.

Interestingly, inhibition of HIV by St. John's Wort extracts has been well studied. The proposed link was that light activated hypericin in the extract produced singlet oxygen that inactivated the virus in some way. However, this related species has similar activity and yet the extract contains no hypericin at all.

REFERENCES

1. Adachi, A., H. E. Gendelman, S. Koenig, T. Folks, R. Willey, A. Rabson, and M. A. Martin. 1986. Production of acquired immunodeficiency syndrome-associated retrovirus in human and nonhuman cells transfected with an infectious molecular clone. J Virol 59:284-91.
2. Hamel, Paul B. and Mary U. Chiltoskey 1975. *Cherokee Plants and Their Uses—A 400 Year History*. Sylva, N.C. Herald Publishing Co. (p. 53)
3. Maury, W., P. J. Wright, and S. Bradley. 2003. Characterization of a cytolytic strain of equine infectious anemia virus. J Virol 77:2385-99.
4. Platt, E. J., K. Wehrly, S. E. Kuhmann, B. Chesebro, and D. Kabat. 1998. Effects of CCR5 and CD4 cell surface concentrations on infections by macrophagetropic isolates of human immunodeficiency virus type 1. J Virol 72:2855-64.
5. Reed-Inderbitzin, E., and W. Maury. 2003. Cellular specificity of HIV-1 replication can be controlled by LTR sequences. Virology 314:680-95.

Example 7

Western Blot Analysis

After an 8 hour treatment with lipopolysaccharide (LPS) and *H. gentianoides* fractions, RAW 264.7 cells were rinsed twice with ice cold 1× phosphate buffered saline (PBS). Lysis buffer (50 mM Tris-HCl, 2 mM EDTA, 2 mM EGTA, 150 mM sodium chloride, 2 mM PMSF, 25 mM leupeptin, 10 mM aprotinin, 10 mM sodium fluoride, 10 mM sodium orthovanadate, 10 mM sodium pyrophosphate, 0.5% Triton X-100) was added to the dishes on ice and the cells were dissociated from the plate by scraping. The lysate was centrifuged at 4° C. and the supernatant was removed. The protein concentration in each lysate was determined using the bicinchonic acid and copper sulfate protein assay (Sigma; St. Louis, Mo.).

For the western blot separation, an equal amount of protein from each lysate (15 µg) was diluted with 2× Laemmli sample buffer [4.0 g sodium dodecyl sulfate (SDS), 25 mL Tris/SDS (6.05 g Tris base, 0.4 g SDS, 25 mL water), 20 mL glycerol, 2 ml β-mercaptanol, 1 mg bromophenol blue, water to 100 ml)] and denatured in a steam bath for 5 min. Separation of the proteins was carried out on a discontinuous (4% stacking, 10% resolving) sodium dodecyl sulfate-polyacrylamide (30% acrylamide/bis solution) (BioRad; Hercules, Calif.) gel, followed by transfer to a PVDF membrane (GE Healthcare; Piscataway, N.J.) at 100V for 2.5 hours. COX-2 rabbit polyclonal antibody (Santa Cruz Biotechnology, Santa Cruz, Calif.) was diluted 1:1000 in 5% milk Tris-buffered saline with 0.5% Tween-20 (TBS-T). The secondary antibody (goat, anti-rabbit IgG, HRP conjugated, Santa Cruz Biotechnology; Santa Cruz, Calif.) was diluted 1:1000 in 5% milk in TBS-T. Detection was visualized on blue sensitive autoradiographic film (Marsh Bioproducts; Rochester, N.Y.) with a chemiluminescence (ECLplus) detection kit (GE Healthcare; Piscataway, N.J.).

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

Example 8

Results

Figure 10:
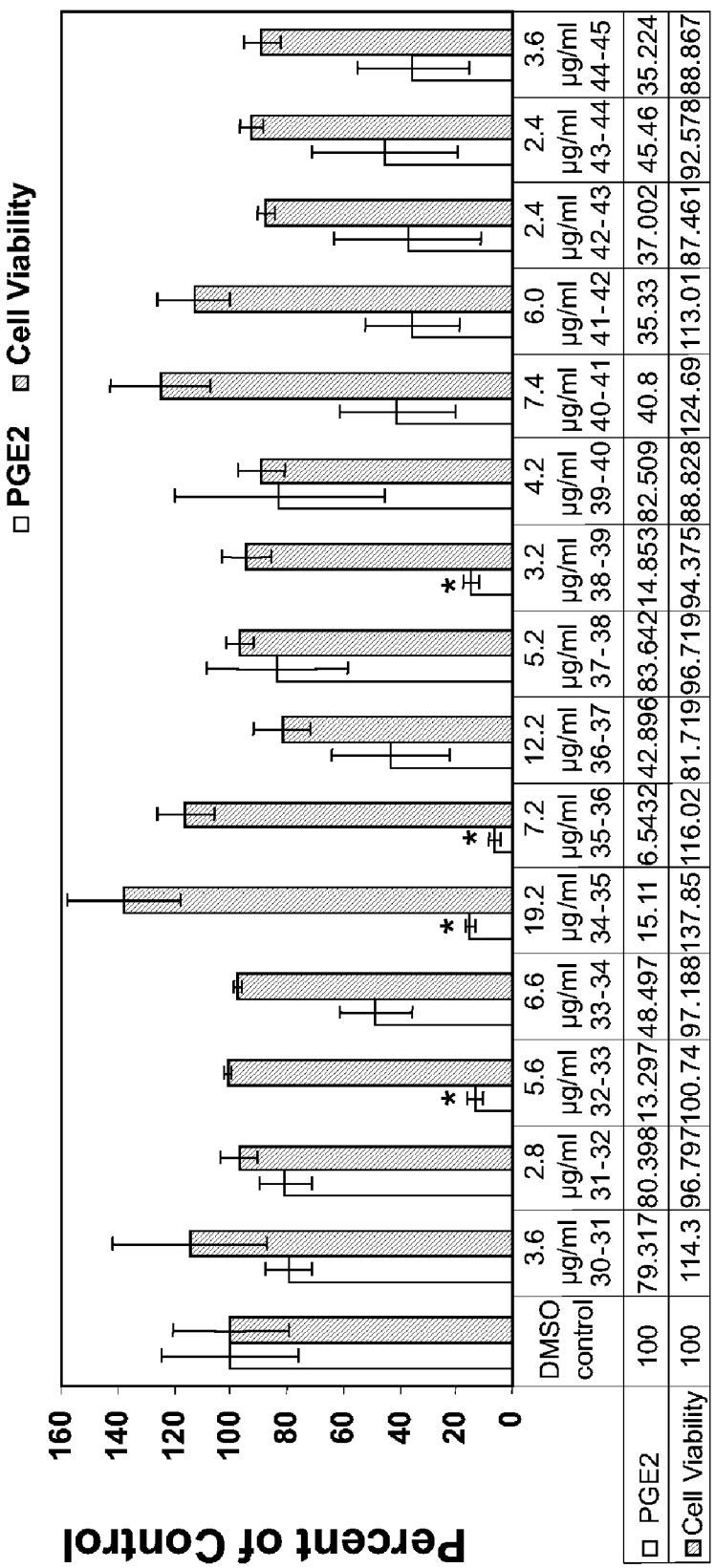
FIG. 10. Four semi-preparative HPLC fractions, from the *H. gentianoides* methanol extract, significantly reduced $PGE_2$ concentrations in LPS-induced macrophages, indicating anti-inflammatory activity. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

Our initial studies found that a methanol extract and fraction 2 from *Hypericum gentianoides* possessed anti-inflammatory properties (1). Further fractionation using the previously described semi-preparative HPLC method produced 15 fractions for $PGE_2$ assay screening (FIG. 10). One of the most anti-inflammatory of these, fraction 32-33 (FIG. 11), significantly reduced $PGE_2$ concentrations by 87% in lipopolysaccharide (LPS)-induced RAW263.7 macrophages at a dose of 5.6 µg/mL (FIG. 1). We further separated fraction 32-33 for $PGE_2$ assays and found fraction 32-32.6 to contain the bioactivity. Fraction 32-32.6 contained two main compounds with 445 m/z being the more abundant (FIG. 3), and was tested for inhibition of cyclooxygenase-1 or cyclooxygenase-2 in LPS-induced macrophages grown in culture. Western blot results indicated that fraction 32-32.6 significantly reduces expression of cyclooxygenase-2, but not cyclooxygenase-1, at a dose of 10 µg/mL (FIG. 4).

Subsequently, peak 445 m/z was further purified for NMR analysis (Supplemental Information). The 2-D NMR experiments provided the data necessary to solve the chemical structure of 445 m/z (FIG. 5) (see also Structure Identification document). The chemical structure was cross-referenced to a previously identified compound, saroaspidin A. However, this compound has never been applied in any assay involving mammalian cells; only antibacterial screening assays (2).

Figure 15:
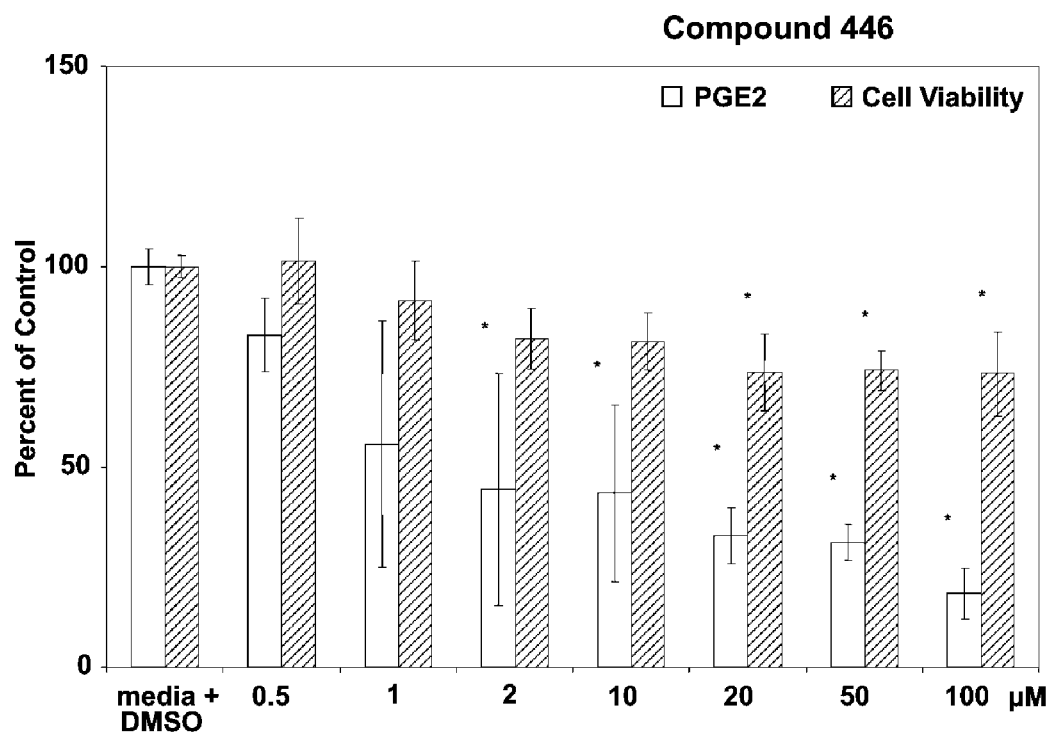
FIG. 15. LPS-induced RAW264.7 macrophages treated with saroaspidin A isolated from *H. gentianoides* have reduced prostaglandin E2 concentrations at doses as low as 2 µM. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

$PGE_2$ assays confirmed that saroaspidin A applied to the LPS-induced macrophages was significantly bioactive at concentrations in the cell culture media as low as 2 µM (FIG. 15).

Figure 14A:
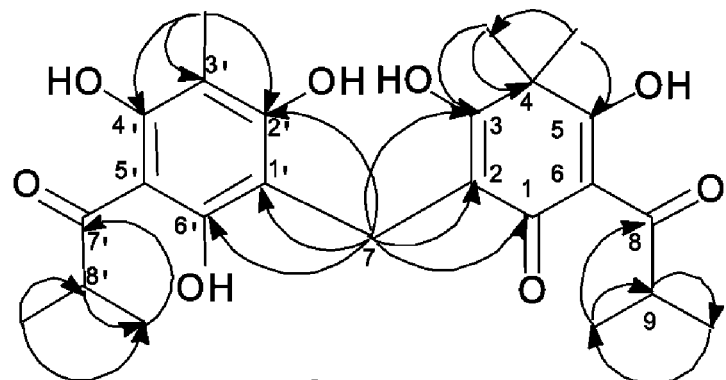
FIG. 14. A.) Two-dimensional NMR spectroscopy observed HMBC correlations confirming the structure of the bioactive compound 446 g/mol with the molecular ion 445 m/z (M-) as saroaspidin A. B.) Two-dimensional NMR spectroscopy observed HMBC correlations supporting the structure of compound 500 g/mol (499 m/z) is that of uliginosin A. Overlapping signals are not shown. C.) Two-dimensional NMR spectroscopy observed HMBC correlations confirming the structure of compound 554 (553 m/z) is that of hyperbrasilol C.
Figure 14B:
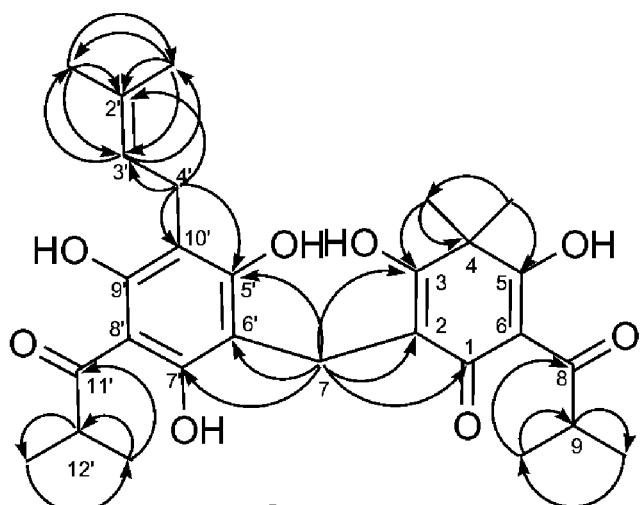
Figure 14C:
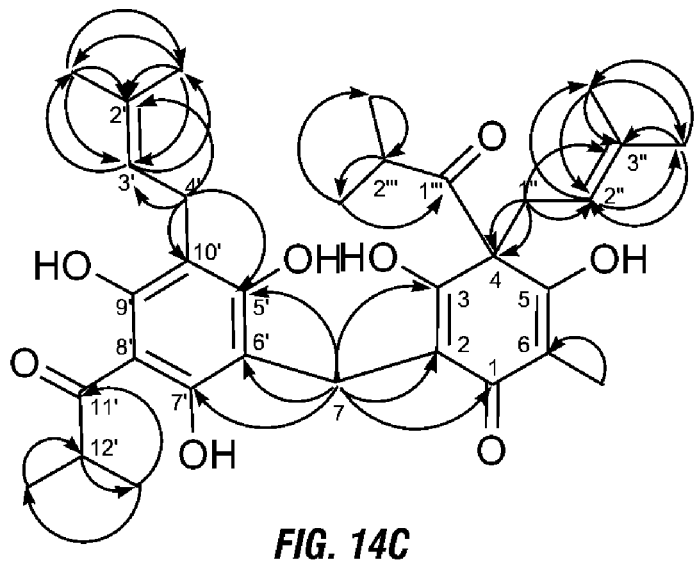
Figure 16:
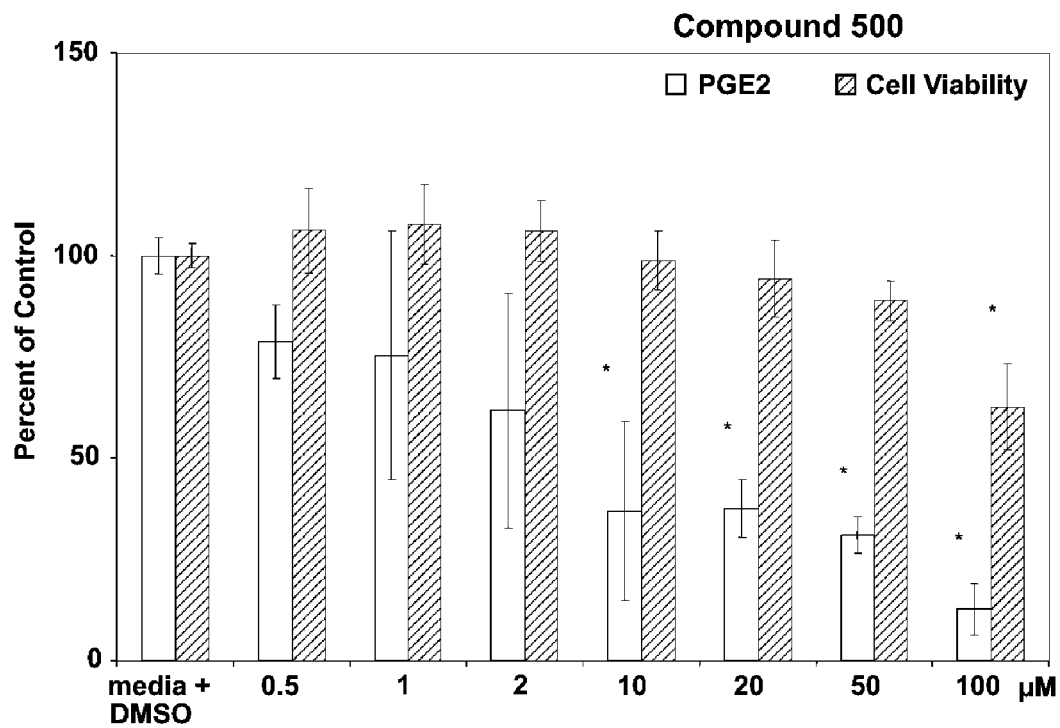
FIG. 16. LPS-induced RAW264.7 macrophages treated with compound 500 g/mol, isolated from *H. gentianoides*, have a significant reduction of prostaglandin E2 concentrations at or above a tested dose of 10 µM in the cell media. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.
Figure 17:
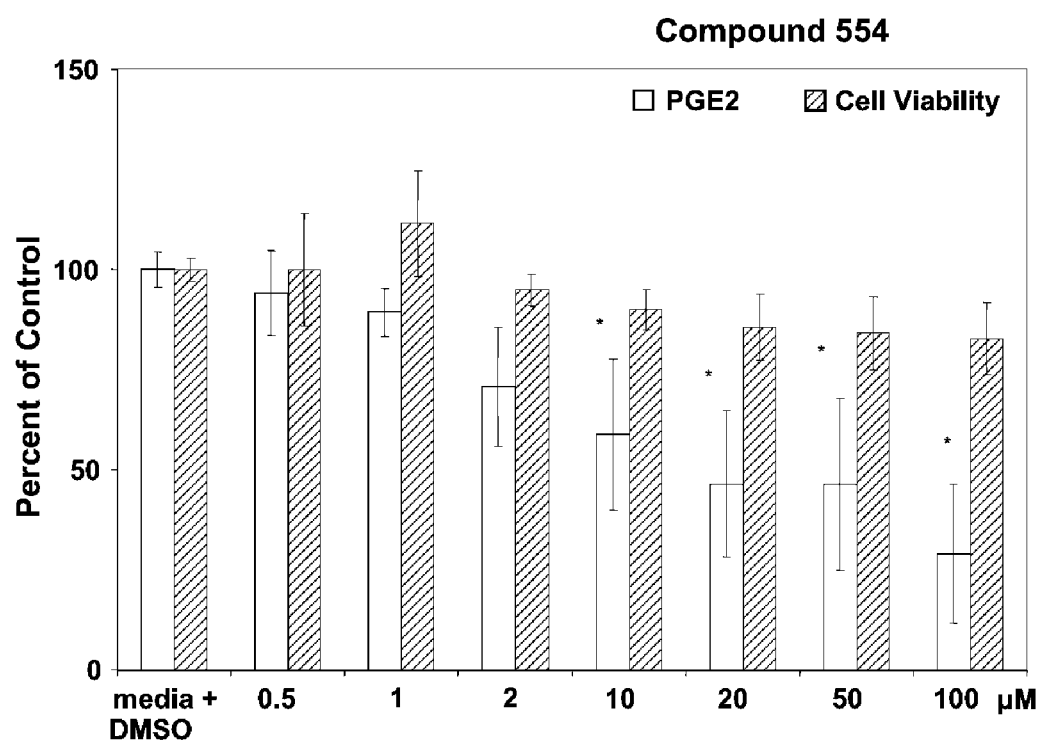
FIG. 17. LPS-induced RAW264.7 macrophages treated with compound 554 g/mol, isolated from *H. gentianoides*, have a significant reduction of prostaglandin E2 concentrations at or above a tested dose of 10 µM in the cell media. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

Another one of the 1 minute fractions, fraction 35-36 also reduced $PGE_2$ concentrations by 93.5% when applied to the media of LPS-induced macrophages, at a dose of 7.2 µg/mL. This fraction contains two compounds with similar abundance, 499 m/z and 553 m/z. These were also purified (Supplemental Information) and their chemical structures solved using 2-D NMR analyses (see also Structure Identification); uliginosin A and hyperbrasilol C (FIG. 14). Both of these compounds, in their pure form, were screened with the $PGE_2$ assay and were capable of significantly reducing $PGE_2$ down to the tested dose of 10 µM (FIGS. 16 and 17). Interestingly, original fractions containing mainly one or the other did not have as great of bioactivity as the two together. This suggests there is a synergistic affect which explains the potent bioactivity when both are applied as a treatment together.

Discussion

All of the data presented indicates that saroaspidin A inhibits $PGE_2$ production in LPS-induced RAW263.7 macrophages. The western blot data shows that saroaspidin A reduces the concentration of the inducible cyclooxygenase-2 (COX-2) in these macrophages during an inflammatory response, while the constitutively expressed cyclooxygenase-1 does not appear to be affected. This suggests that saroaspidin A is selectively inhibiting COX-2, a target for treating chronic inflammatory diseases. Furthermore, there are other dimeric phloroglucinols in *H. gentianoides* that have anti-inflammatory activity, and results suggest there are synergistic effects when certain combinations of these are applied for treating inflammatory responses. There are conserved structures amongst all three isolated bioactive compounds (FIG. 16). However, saroaspidin A more potently inhibits COX-2; suggesting $R_1$ being an isobutyryl group and $R_4$ being a methyl group is important to the increased bioactivity.

FIG. 10 depicts four semi-preparative HPLC fractions, from the *H. gentianoides* methanol extract, significantly reduced $PGE_2$ concentrations in LPS-induced macrophages, indicating anti-inflammatory activity. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

Molecular Ion Mass Spectra

Figure 11:
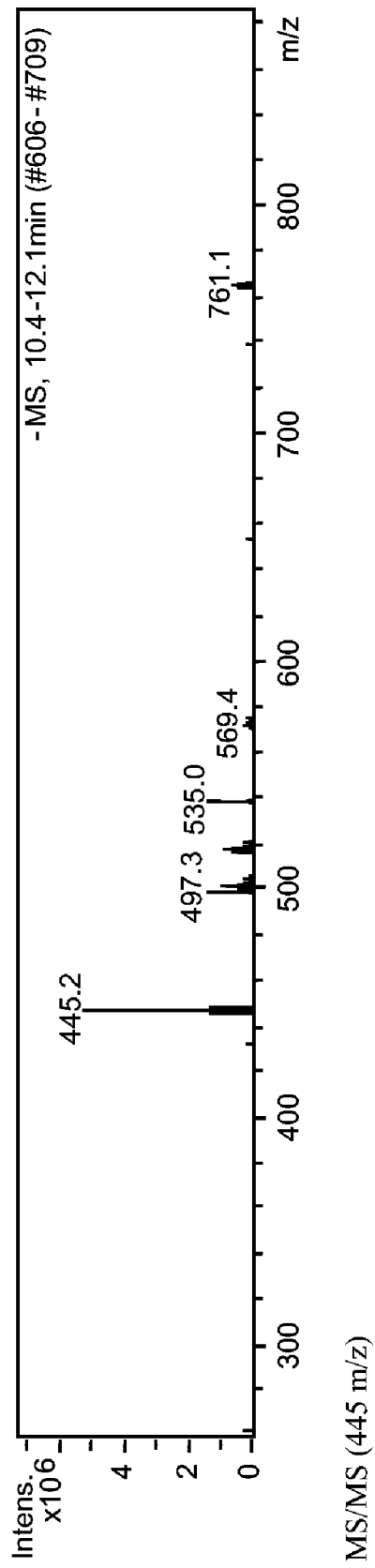
FIG. 11. Molecular Ion Mass Spectra: Fraction 32-33 LC-ESI-MS molecular ion and MS/MS data.
Figure 11:
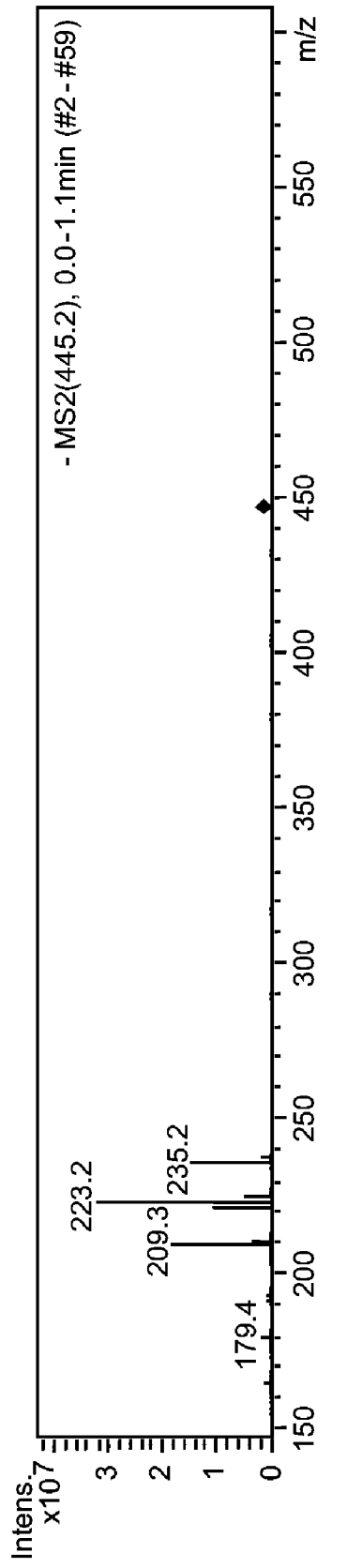

FIG. 11. Fraction 32-33 LC-ESI-MS molecular ion and MS/MS data.

Figure 12:
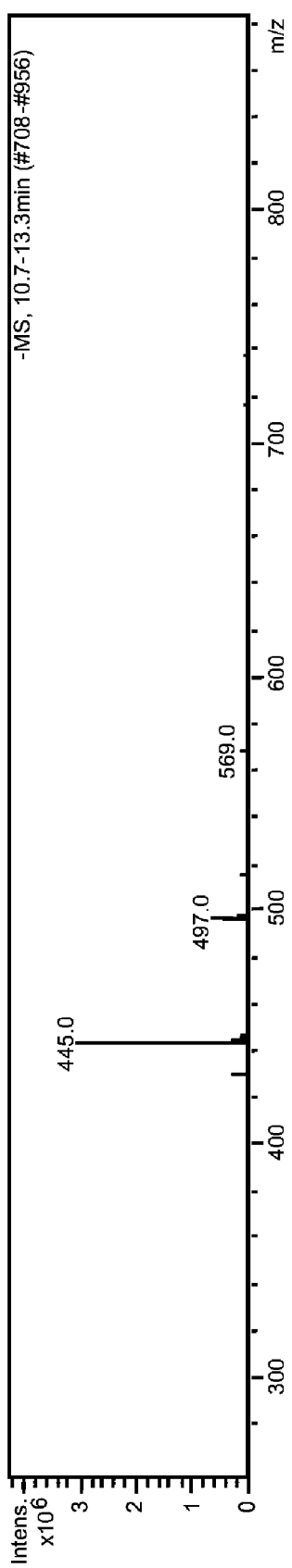
FIG. 12. Molecular Ion Mass Spectra: Fraction 32-32.6 LC-ESI-MS molecular ion data.

FIG. 12. Fraction 32-32.6 LC-ESI-MS molecular ion data.

Figure 13:
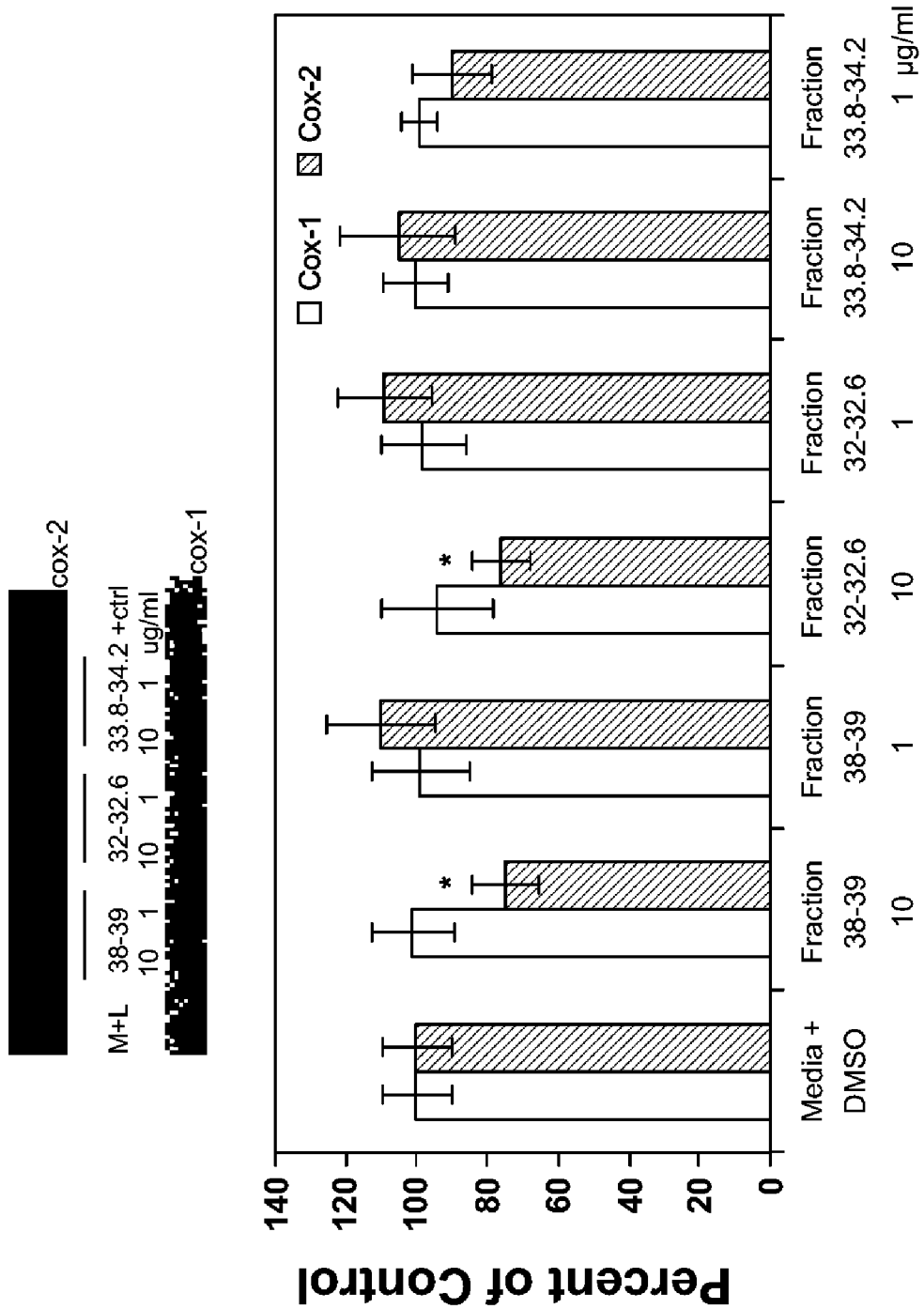
FIG. 13. Quantified western blot. Cyclooxygenase-2 is significantly reduced in RAW263.7 macrophages treated with the 32-32.6 fraction compared to the control. This suggests a specific interaction affecting the inducible cyclooxygenase-2 after the LPS induced inflammation response while the constitutively expressed cyclooxygenase-1 is unaffected.

FIG. 13. Quantified western blot. Cyclooxygenase-2 is significantly reduced in RAW263.7 macrophages treated with the 32-32.6 fraction compared to the control. This suggests a specific interaction affecting the inducible cyclooxygenase-2 after the LPS-induced inflammation response while the constitutively expressed cyclooxygenase-1 is unaffected. Control: No difference in COX-2 protein level without LPS (media+DMSO vs. treatments); No difference in COX-1 protein level without LPS (media+DMSO vs. treatments). Treatments replicated 3 times (1 blot/treatment) and normalized by blot to positive control for consistency.

FIG. 14. A.) Two-dimensional NMR spectroscopy observed HMBC correlations confirming the structure of the bioactive compound 446 g/mol with the molecular ion 445 m/z (M-) as saroaspidin A. B.) Two-dimensional NMR spectroscopy observed HMBC correlations supporting the structure of compound 500 g/mol (499 m/z) is that of uliginosin A. Overlapping signals are not shown. C.) Two-dimensional NMR spectroscopy observed HMBC correlations confirming the structure of compound 554 (553 m/z) is that of hyperbrasilol C.

FIG. 15. LPS-induced RAW264.7 macrophages treated with saroaspidin A isolated from *H. gentianoides* have reduced prostaglandin E2 concentrations at doses as low as 2 µM. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

FIG. 16. LPS-induced RAW264.7 macrophages treated with compound 500 g/mol, isolated from *H. gentianoides*, have a significant reduction of prostaglandin E2 concentrations at or above a tested dose of 10 µM in the cell media. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

FIG. 17. LPS-induced RAW264.7 macrophages treated with compound 554 g/mol, isolated from *H. gentianoides*, have a significant reduction of prostaglandin E2 concentrations at or above a tested dose of 10 µM in the cell media. Anti-inflammatory activity is given as mean percent of (media+DMSO+LPS $PGE_2$ level±standard error) and cytotoxicity is given as mean percent of (media+DMSO cell viability±standard error) for *H. gentianoides* fractions (n=4 for each). * p-value less than 0.05 as compared to control.

FIG. 18. Conserved structural regions amongst saroaspidin A, uliginosin A, and hyperbrasilol C. The left ring system is defined as an acyl-phloroglucinol and portion highlighted in red is conserved between all three compounds. The right ring system is defined as a filicinic acid moiety with a ketoacyl group located at $R_1$ or $R_2$ or $R_3$; and the portion highlighted in blue is also conserved amongst all three compounds. These two rings are bonded together by a methylene bridge, which is itself a conserved chemical structure. In saroaspidin A and uliginosin A, $R_1$ is an isobutyryl group.

Supplemental Information

Figure 19:
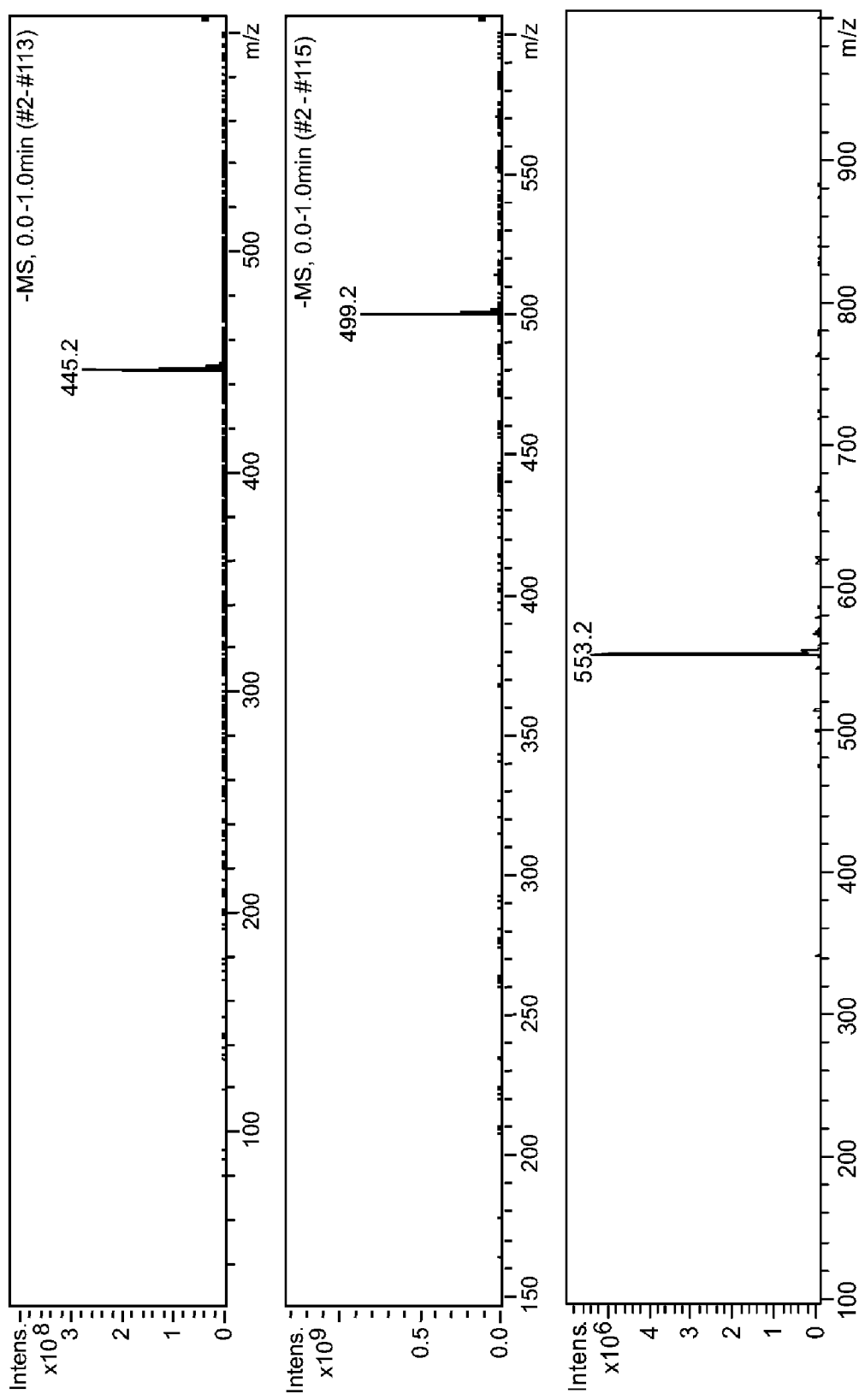
FIG. 19 shows purified Compounds Mass Spectra.

FIG. 19 shows purified Compounds Mass Spectra.

REFERENCES

1. Hillwig, M. L.; Hammer, K. D. P.; Birt, D. F.; Wurtele, E. S. Characterizing the Novel Metabolic Fingerprint and Antiinflammatory Activity of *Hypericum gentianoides*. Journal of Agricultural and Food Chemistry. 2008 (accepted).
2. Ishiguro, K.; Yamaki, M.; Kashihara, M.; Takagi, S. Saroaspidin A, B, and C: additional antibiotic compounds from *Hypericum japonicum*. Planta Medica. 1987, 53, 415-7.

Example 9

Identification of an Anti-Inflammatory Prostaglandin E2 ($PGE_2$) Reducing Compounds from a *Hypericum gentianoides* Extract Reported herein is the most bioactive prostaglandin E2 ($PGE_2$) reducing compound from a *Hypericum gentianoides* organic solvent metabolite extract. Previous results indicated certain semi-preparative HPLC fractions, prepared from a *H. gentianoides* extract significantly reduced the concentration of $PGE_2$ in lipo-polysachamide (LPS)-induced RAW264.7 macrophages growing in cell culture. This is an indicator of anti-inflammatory activity. In particular, fraction 32-32.6 was of particular interest because of the ability of fraction 32-32.6 to reduce $PGE_2$ concentrations at the lowest dose applied to the growth medium, 1 µg/mL.

Liquid chromatography-mass spectrometry (LC-MS) analytical analysis, using an Agilent Ion Trap 1100, showed fraction 32-32.6 contained one major compound with a dimeric chemical structure with a molecular ion with a 445 mass-to-charge ratio (m/z) in negative ion mode, suggesting a molecular weight of approximately 446 g/mol. Further purification with semi-preparative HPLC of fraction 32-32.6 lead to the isolation of 2 mg of the pure compound from 30 g of the original dry plant material.

Figure 20:
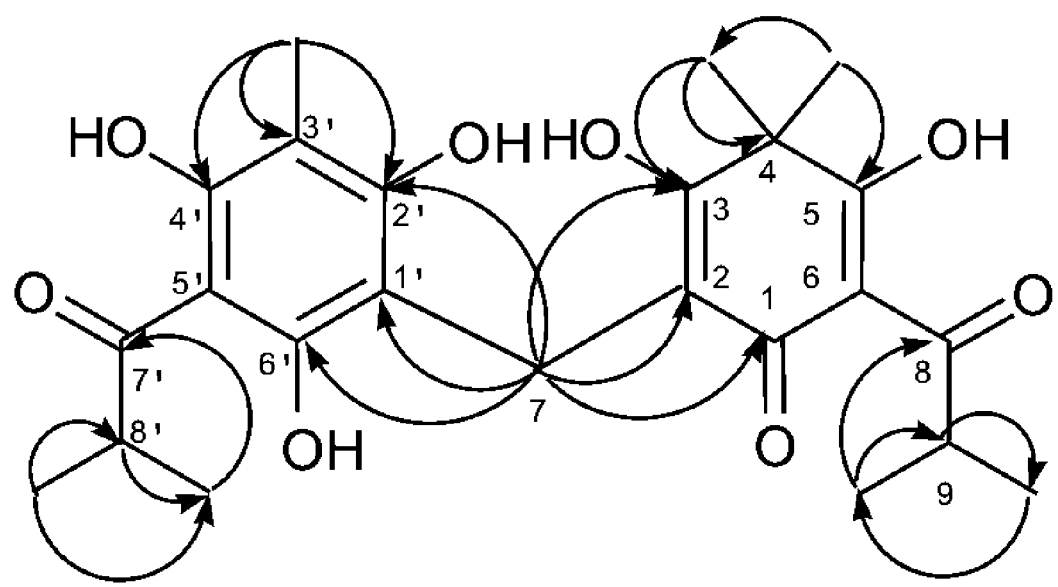
FIG. 20. Two-dimensional NMR spectroscopy observed HMBC correlations confirming the structure of the bioactive compound 446 as saroaspidin A. Overlapping signals are not shown.

Using two-dimensional nuclear magnetic resonance (NMR) spectroscopy experiments including heteronuclear multiple bond correlation (HMBC), double-quantum filtered correlation spectroscopy (dqfCOSY), and heteronuclear single quantum correlation (HSQC), the applicant elucidated the chemical structure of the compound of interest (FIG. 20). The compound is saroaspidin A. This compound was previously identified in *Hypericum japonicum* (1). The compound contains a phloroglucinol moiety and a filicinic acid moiety. Saroaspidin A has never been tested on any mammalian cells for any bioactivity including anti-inflammatory activity, it has only been tested in an antibacterial screening assay (1).

Figure 21:
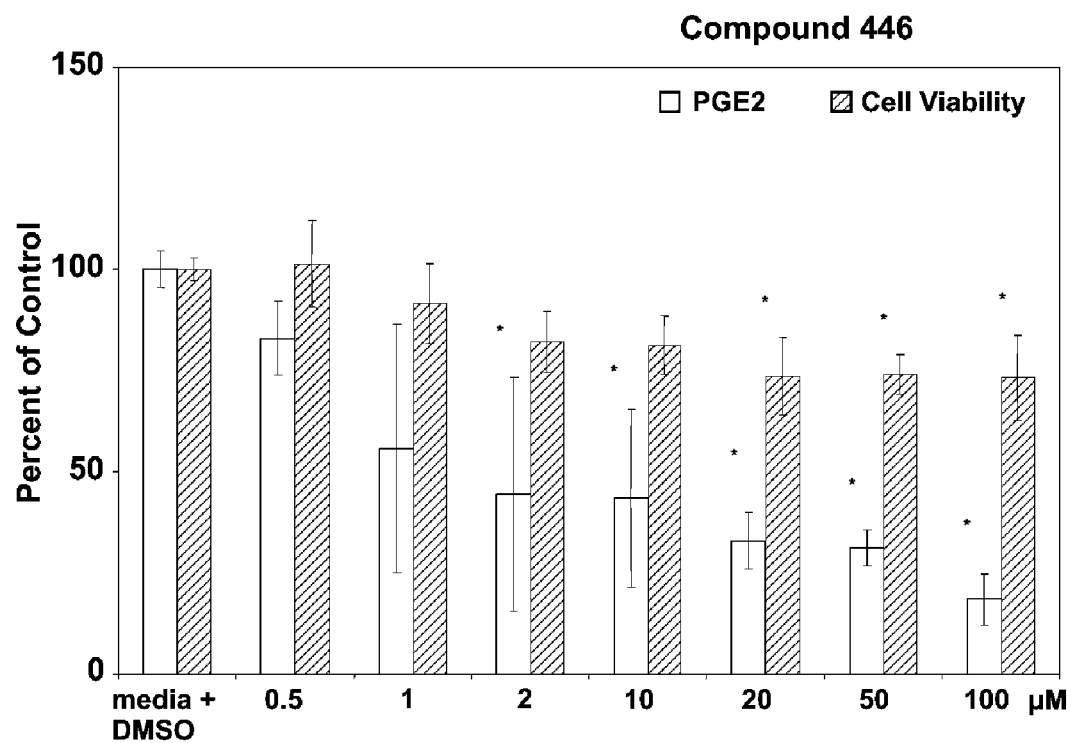
FIG. 21. Lipopolysachamide-induced RAW264.7 macrophages treated with saroaspidin A isolated from *H. gentianoides* have reduced prostaglandin E2 concentrations at doses as low as 2 µM.

The purified saroaspidin A was tested in the same anti-inflammatory model as previously described for the *H. gentianoides* extract and fractions tested (2). Different dilutions of the compound at 0.5, 1, 2, 10, 20, 50, and 100 µM concentrations, and 1 µg/ml of the LPS inflammation inducer, were applied simultaneously to the growth medium of RAW264.7 macrophages in 24-well plates. (The *limulus* (LAL) test was performed to ensure LPS was not present in the cell cultures prior to treatments). Eight hours later cells were collected and the concentration of $PGE_2$ was measured. Results indicate that the application of saroaspidin A significantly reduced $PGE_2$ concentrations down to an applied dose of 2 µM compared to the control (FIG. 21). Significant cytotoxicity stops at doses of 10 µM or lower.

Figure 22:
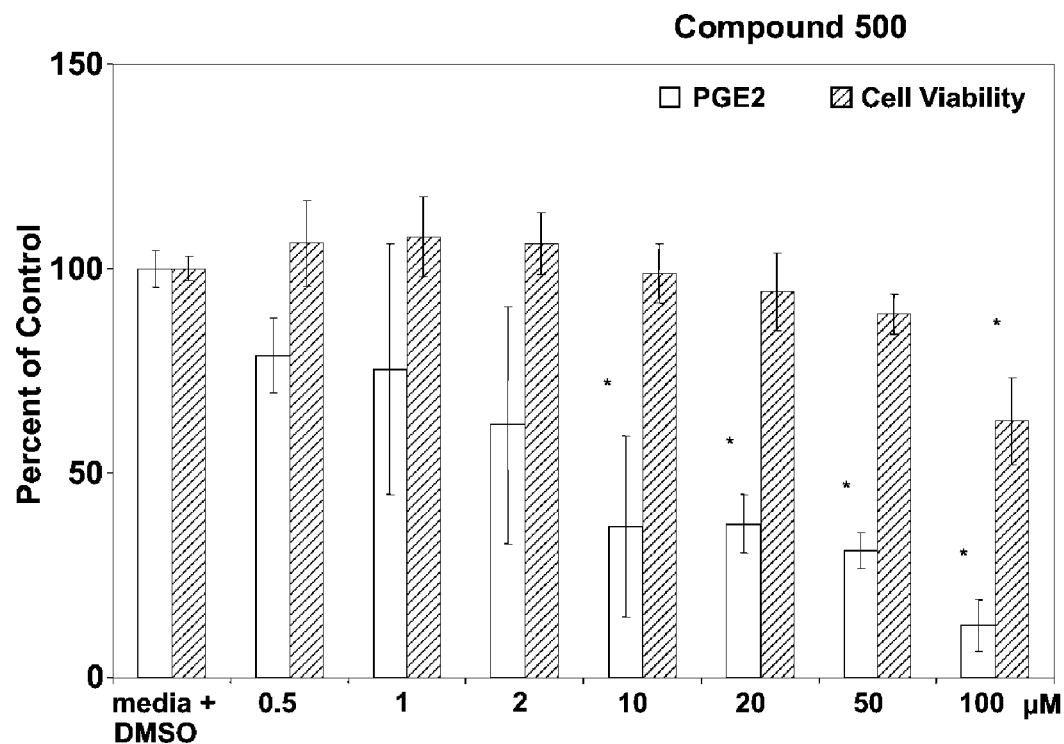
FIG. 22. Lipopolysachamide-induced RAW264.7 macrophages treated with compound 500 g/mol, isolated from *H. gentianoides*, have a significant reduction of prostaglandin E2 concentrations at or above a tested dose of 10 µM in the cell media.
Figure 23:
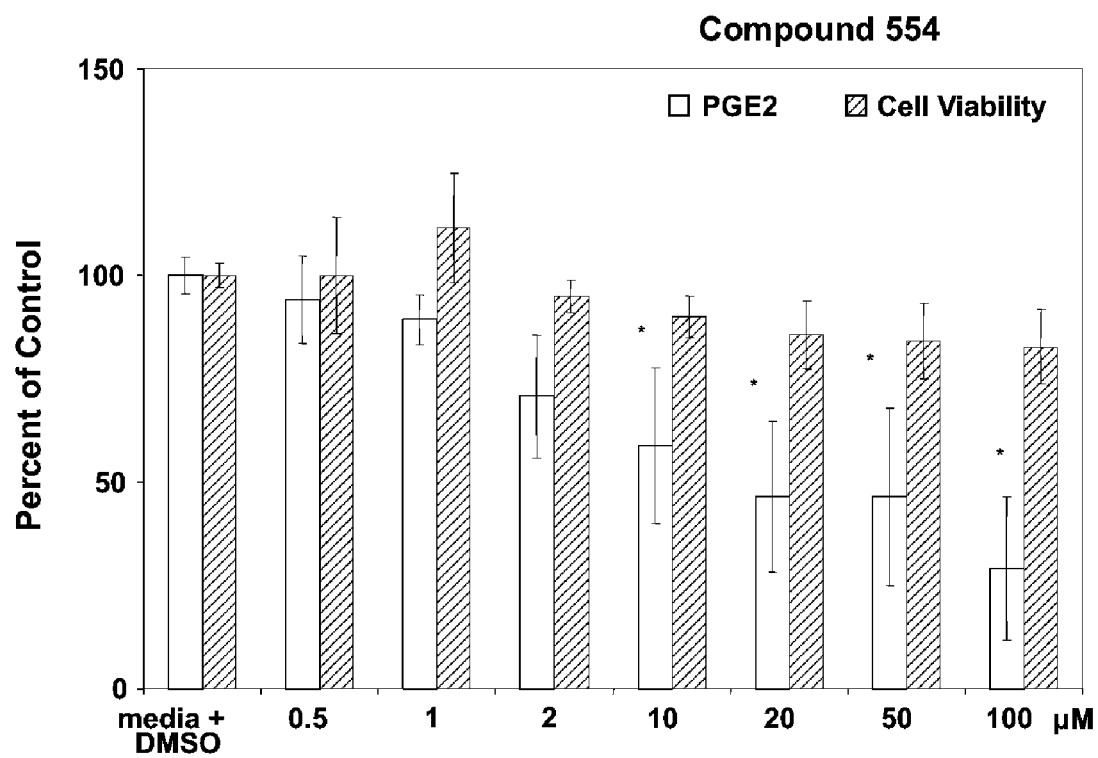
FIG. 23. Lipopolysachamide-induced RAW264.7 macrophages treated with compound 554 g/mol, isolated from *H. gentianoides*, have a significant reduction of prostaglandin E2 concentrations at or above a tested dose of 10 µM in the cell media.
Figure 24:
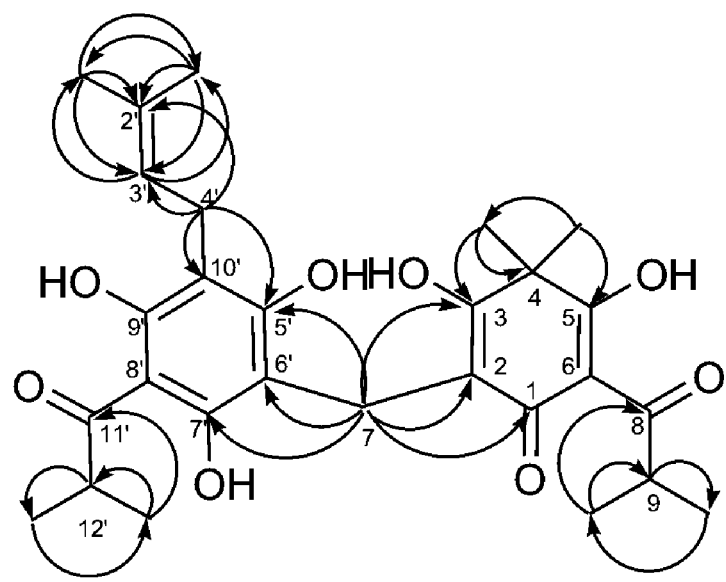
FIG. 24. Two-dimensional NMR spectroscopy observed HMBC correlations supporting the structure of compound 500 is that of uliginosin A.
Figure 25:
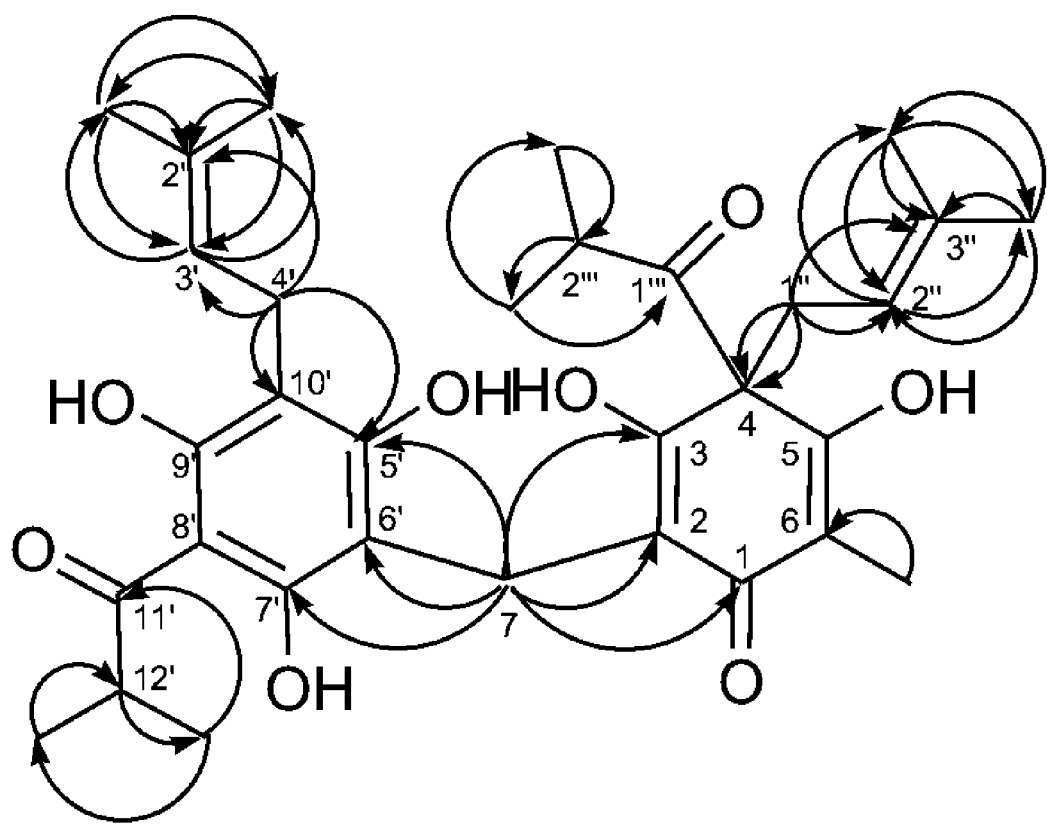
FIG. 25. Two-dimensional NMR spectroscopy observed HMBC correlations confirming the structure of compound 554 is that of hyperbrasilol C.

Other compounds from the *H. gentianoides* extract also demonstrated anti-inflammatory bioactivity. Two other purified compounds from *H. gentianoides* have been tested for $PGE_2$ reducing bioactivity in the same aforementioned anti-inflammatory assay. These showed a significant $PGE_2$ reduction down to the tested dose of 10 µM (FIGS. 22 and 23). Conversely, compound 554 shows no significant cytotoxicity even at a dose of 100 µM and compound 500 shows no significant cytotoxicity until the tested dose of 100 µM. Compounds 500 and 554 have been tentatively identified as uliginosin A (500) and hyperbrasilol C (554), both of which are structurally similar to saroaspidin A (3). The HMBC correlations are shown in FIGS. 24 and 25, with spectral data in Tables 2 and 3. These compounds also contain phloroglucinol moieties and a filicinic acid moieties. The exact mass of the three molecular ions of these compounds were also determined using an ABI LC/MS-Q Star tandem mass specta-time of flight spectrometer. The exact mass of the molecular ions in negative mode were: 445.2174 m/z, 499.2587 m/z, 553.3017 m/z. These values support the chemical formulas of saroaspidin A ($C_{24}H_{30}O_8$), uliginosin A ($C_{28}H_{36}O_8$), and hyperbrasilol C($C_{32}H_{42}O_8$) when the mass of a proton is added back to the molecular ion exact mass; yielding the molecular exact mass.

In conclusion, three compounds have been identified from the organic solvent extract of *H. gentianoides* plant material which possess anti-inflammatory activity as measured by reduced $PGE_2$ concentrations in LPS-induced RAW264.7 macrophages.

FIG. 20. Two-dimensional NMR spectroscopy observed HMBC correlations confirming the structure of the bioactive compound 446 as saroaspidin A. Overlapping signals are not shown.

TABLE 1

Spectral Data for compound 446.

| C | chemical shift (ppm) | H' | chemical shift(ppm) |
|---|---|---|---|
| 1 | 184 | | |
| 2 | 105 | | |
| 3 | 195 | 3-OH | 16.44 |
| 4 | 52 | 4-Me | 1.26 |
| 4-Me | 24 | 5-OH | 16.44 |
| 5 | 201 | | |
| 6 | n.o. | | |
| 7 | 17.3 | 7 | 3.48 |
| 8 | 211 | | |
| 9 | 38.4 | 9 | 4.18 |
| 9-Me | 18.5 | 9-Me | 1.16 |
| 1' | 107.5 | | |
| 2' | 161.5 | 2'-OH | n.o. |
| 3' | 103 | | |
| 3'-Me | 21 | 3'-Me | 1.97 |
| 4' | 161.5 | 4'-OH | n.o. |
| 5' | n.o. | | |
| 6' | 157 | 6'-OH | n.o. |
| 7' | 199.7 | | |
| 8' | 33.8 | 8' | 3.92 |
| 8'-Me | 18.3 | 8'-Me | 1.13 |

FIG. 21. Lipopolysachamide-induced RAW264.7 macrophages treated with saroaspidin A isolated from *H. gentianoides* have reduced prostaglandin E2 concentrations at doses as low as 2 µM.

FIG. 22. Lipopolysachamide-induced RAW264.7 macrophages treated with compound 500 g/mol, isolated from *H. gentianoides*, have a significant reduction of prostaglandin E2 concentrations at or above a tested dose of 10 µM in the cell media.

FIG. 23. Lipopolysachamide-induced RAW264.7 macrophages treated with compound 554 g/mol, isolated from *H. gentianoides*, have a significant reduction of prostaglandin E2 concentrations at or above a tested dose of 10 µM in the cell media.

FIG. 24. Two-dimensional NMR spectroscopy observed HMBC correlations supporting the structure of compound 500 is that of uliginosin A.

TABLE 2

Spectral Data for compound 500 g/mol.

| C | 499.2587 m/z | H' | 499.2587 m/z |
|---|---|---|---|
| 1 | 194.5 | | |
| 2 | 105.4 | | |
| 3 | 184.5 | 3-OH | n.o. |
| 4 | 49.9 | | |
| 4-Me | 56.5 | 4-Me | 1.23 |
| 5 | 197.5 | 5-OH | 19.32 |
| 6 | 111.9 | | |
| 7 | 18 | 7 | 3.5 |
| 8 | 210.7 | | |
| 9 | 38.5 | 9 | 4.15 |
| 9-Me | 18.6 | | 1.17 |
| 2' | 129.7 | | |
| 2'-Me | 16.5 | 2'-Me | 1.65 |
| " | 24.6 | " | 1.76 |
| 3' | 123.1 | 3' | 5.1 |
| 4' | 21.3 | 4' | 3.26 |
| 5' | 160.8 | 5-OH | n.o. |
| 6' | 107.6 | | |
| 7' | 157.7 | 7'-OH | 13.84 |
| 8' | 106.9 | | |
| 9' | 160.8 | 9'-OH | n.o. |
| 10' | 107.6 | | |
| 11' | 199.9 | | |
| 12' | 33.5 | 12' | 3.55 |
| 12'-Me | 18.6 | 12'-Me | 1.14 |

FIG. 25. Two-dimensional NMR spectroscopy observed HMBC correlations confirming the structure of compound 554 is that of hyperbrasilol C.

TABLE 3

Spectral Data for compound 554 g/mol.

| C | 553.3017 m/z | H' | 553.3017 m/z |
|---|---|---|---|
| 1 | 193.2 | | |
| 2 | 107 | | |
| 3 | 184.5 | 3-OH | n.o. |
| 4 | 48.8 | | |
| 5 | 193.2 | 5-OH | 19.33 |
| 6 | 115.7 | | |
| 6-Me | 19.2 | 6-Me | 1.93 |
| 7 | 16.7 | 7 | 3.47 |
| 2' | 129.7 | | |
| 2'-Me | 16.5 | 2'-Me | 1.57 |
| " | 24.5 | | 1.7 |
| 3' | 123.2 | 3' | 5.11 |
| 4' | 21.4 | 4' | 3.2 |
| 5' | 160.8 | 5-OH | 9.62 |
| 6' | 107.7 | | |
| 7' | 157.4 | 7'-OH | 9.62 |
| 8' | n.o. | | |
| 9' | n.o. | 9'-OH | 9.62 |
| 10' | 107.7 | | |
| 11' | 199.9 | | |
| 12' | 33.5 | 12' | 3.92 |
| 12'-Me | 18.6 | 12'-Me | 1.1 |
| 1" | n.o. | 1" | 3.19 |
| | | | 3.4 |
| 2" | 123.2 | 2" | 5.11 |
| 3" | 129.7 | | |
| 3"-Me | 16.5 | 3"-Me | 1.57 |
| " | 24.5 | " | 1.7 |
| 1'" | 210.8 | | |
| 2'" | 39.1 | 2'" | 4.19 |
| 2'"-Me | 18.6 | 2'"-Me | 1.08 |

REFERENCES

1. Ishiguro, K.; Yamaki, M.; Kashihara, M.; Takagi, S. Saroaspidin A, B, and C: additional antibiotic compounds from *Hypericum japonicum*. Planta Medica. 1987, 53, 415-7.
2. Hammer, K. D. P.; Hillwig, M. L.; et al. Inhibition of prostaglandin E2 production by anti-inflammatory *Hypericum perforatum* extracts and constituents in RAW264.7 mouse macrophage cells. Journal of Agricultural and Food Chemistry. 2007, 55, 7323-7331.
3. Rocha, L.; Marston, A.; Potterat, O.; Kaplan, M. A. C.; Hostettmann, K. More phloroglucinols from *Hypericum brasiliense*. Phytochemistry. 1996, 42, (1), 185-188.

What is claimed is:

1. A method of treating inflammation in an animal comprising: administering to an animal in need thereof, an effective amount of an isolated acyl-phloroglucinol selected from the group consisting of saroaspidin A, uliginosin A and hyperbrasilol C.

2. The method of claim 1 wherein said acyl-phloroglucinol is isolated from a plant.

3. The method of claim 2 wherein said acyl-phloroglucinol is isolated from a plant of the genus *Hypericum*.

4. The method of claim 3 wherein said acyl-phloroglucinol is isolated from *Hypericum gentianoides*.

5. The method of claim 1 wherein said treatment for inflammation includes treatment for joint inflammation.

* * * * *

UNITED STATES PATENT AND TRADEMARK OFFICE
Certificate

Patent No. 7,854,946 B1                                                                                             Patented: December 21, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Matthew Lee Hillwig, Ames, IA (US); and Eve Syrkin Wurtele, Ames, IA (US).

Signed and Sealed this Twelfth Day of February 2013.

TERRY A. MCKELVEY
                                                                                        *Supervisory Patent Examiner*
                                                                                                   Art Unit 1655
                                                                                      Technology Center 1600